(12) United States Patent
Tomita et al.

(10) Patent No.: US 10,888,840 B2
(45) Date of Patent: Jan. 12, 2021

(54) MATERIAL FOR REMOVING ACTIVATED LEUKOCYTE-ACTIVATED PLATELET COMPLEX

(71) Applicant: TORAY INDUSTRIES, INC., Tokyo (JP)

(72) Inventors: Naotoshi Tomita, Otsu (JP); Kaoru Shimada, Otsu (JP); Hiroshi Takahashi, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 16/615,295

(22) PCT Filed: Jun. 6, 2018

(86) PCT No.: PCT/JP2018/021655
§ 371 (c)(1),
(2) Date: Nov. 20, 2019

(87) PCT Pub. No.: WO2018/225764
PCT Pub. Date: Dec. 13, 2018

(65) Prior Publication Data
US 2020/0197594 A1    Jun. 25, 2020

(30) Foreign Application Priority Data
Jun. 6, 2017 (JP) .................. 2017-111404

(51) Int. Cl.
| | | |
|---|---|---|
| *B01J 20/28* | (2006.01) | |
| *B01J 20/26* | (2006.01) | |
| *A61M 1/36* | (2006.01) | |
| *B01D 15/38* | (2006.01) | |
| *B01J 20/288* | (2006.01) | |

(52) U.S. Cl.
CPC ........ *B01J 20/28023* (2013.01); *A61M 1/362* (2014.02); *B01D 15/3823* (2013.01); *B01J 20/265* (2013.01); *B01J 20/288* (2013.01); *B01J 20/28054* (2013.01); *A61M 2202/0427* (2013.01); *A61M 2202/0439* (2013.01); *A61M 2202/0447* (2013.01); *A61M 2202/07* (2013.01); *B01J 2220/50* (2013.01)

(58) Field of Classification Search
CPC ............... A61M 1/362; A61M 1/3679; A61M 2202/0427; A61M 2202/0439; A61M 2202/0447; A61M 2202/07; B01D 15/3823; B01J 20/265; B01J 20/28; B01J 20/28023; B01J 20/28054; B01J 20/288; B01J 20/50
See application file for complete search history.

(56) References Cited

U.S. PATENT DOCUMENTS

| | | |
|---|---|---|
| 5,407,581 A | 4/1995 | Onodera et al. |
| 6,260,715 B1 | 7/2001 | Simard et al. |
| 9,127,250 B2 | 9/2015 | Ogasawara et al. |
| 2004/0226874 A1 | 11/2004 | Nanko et al. |
| 2005/0063935 A1 | 3/2005 | Hirai et al. |
| 2013/0220912 A1 | 8/2013 | Tomita et al. |
| 2019/0184371 A1 | 6/2019 | Kanda et al. |

FOREIGN PATENT DOCUMENTS

| | | |
|---|---|---|
| EP | 0819439 A1 | 1/1998 |
| EP | 1439212 A1 | 7/2004 |
| EP | 2223712 A1 | 9/2010 |
| EP | 2633872 A1 | 9/2013 |
| JP | 5-168706 A | 7/1993 |
| JP | 8-281100 A | 10/1996 |
| JP | 10-147518 A | 6/1998 |
| JP | 2003-201251 A | 7/2003 |
| JP | 2006-312604 A | 11/2006 |
| JP | 4035191 B2 | 1/2008 |
| JP | 4224621 B2 | 2/2009 |
| JP | 2009-95436 A | 5/2009 |
| JP | 2009-254695 A | 11/2009 |
| JP | 4591974 B2 | 12/2010 |
| JP | 2011-145 A | 1/2011 |
| JP | 2011-194014 A | 10/2011 |
| JP | 5824873 B2 | 12/2015 |
| JP | 2016-77466 A | 5/2016 |
| WO | WO 2012/033522 A1 | 3/2012 |
| WO | WO 2012/057185 A1 | 5/2012 |
| WO | WO 2012/094571 A1 | 7/2012 |
| WO | WO 2012/133399 A1 | 10/2012 |

OTHER PUBLICATIONS

Extended European Search Report, dated May 18, 2020, for European Application No. 18814124.6.
Sáez-Gonzalez et al., "Immunological Mechanisms of Adsorptive Cytapheresis in Infammatory Bowel Disease," vol. 62, No. 6, Digestive Diseases and Science, Springer, NY LLC, US, Apr. 21, 2017, XP036242934, pp. 1417-1425.
International Search Report, issued in PCT/JP2018/021655, PCT/ISA/210, dated Sep. 11, 2018.
Written Opinion of the International Searching Authority, issued in PCT/JP2018/021655, PCT/ISA/237, dated Sep. 11, 2018.

(Continued)

*Primary Examiner* — John Kim
(74) *Attorney, Agent, or Firm* — Birch, Stewart, Kolasch & Birch, LLP

(57) ABSTRACT

An object of the present invention is to provide a material which can remove an activated leukocyte-activated platelet complex with high efficiency. The present invention provides a material for removing an activated leukocyte-activated platelet complex, the material being a water-insoluble carrier to the surface of which carrier a compound(s) having a charged functional group(s) is(are) bound, wherein an extending length ratio of the surface is 4 to 7.

9 Claims, 2 Drawing Sheets

(56) References Cited

OTHER PUBLICATIONS

Extended European Search Report for European Application No. 17848867.2, dated Nov. 20, 2019.
Hack et al., "Interleukin-8 in Sepsis: Relation to Shock and Inflammatory Mediators," Infection and Immunity, vol. 60, No. 7, Jul. 1992, pp. 2835-2842.
International Search Report for International Application No. PCT/JP2017/032397, dated Dec. 5, 2017.
Nakada et al., "Continuous Hemodiafiltration with PMMA Hemofilter in the Treatment of Patients with Septic Shock," Mol. Med., vol. 14, No. 5-6, May-Jun. 2008, pp. 257-263.
Oda et al., "Sequential measurement of IL-6 blood levels in patients with systemic inflammatory response syndrome (SIRS)/sepsis," Cytokine, vol. 29, 2005, pp. 169-175.
Written Opinion of the International Searching Authority for International Application No. PCT/JP2017/032397, dated Dec. 5, 2017.
Zarbock et al., "Complete reversal of acid-induced acute lung injury by blocking of platelet-neutrophil aggregation," The Journal of Clinical Investigation, vol. 116, No. 12, Dec. 2006, pp. 3211-3219.

MATERIAL FOR REMOVING ACTIVATED LEUKOCYTE-ACTIVATED PLATELET COMPLEX

TECHNICAL FIELD

The present invention relates to a material for removing an activated leukocyte-activated platelet complex.

BACKGROUND ART

Humoral factors such as inflammatory cytokines are deeply involved in etiology of inflammatory diseases such as systemic lupus erythematosus, rheumatoid arthritis, multiple sclerosis, ulcerative colitis and Crohn's disease, and an attempt has been made to treat the inflammatory diseases by inactivating these humoral factors using low molecular weight pharmaceuticals, biopharmaceuticals such as antibodies, or the like. However, these humoral factors do not act on an inflamed site on its own, but a plurality of humoral factors act synergistically to cause the inflammatory diseases to develop and progress. Thus, recent interest has focused on an extracorporeal circulation therapy using a material which can remove not only humoral factors but also cells themselves, such as activated leukocytes or platelets, which are sources of the humoral factors from a living body.

In recent years, as a new causative substance of inflammatory diseases, an activated leukocyte-activated platelet complex is drawing attention. It is reported that the activated leukocyte-activated platelet complex has a higher chemotactic activity to tissues exhibiting an inflammatory reaction and releases more histotoxic substances compared with an activated leukocytes alone, and that the interaction between an activated platelet and an activated leukocyte enhances the release of histotoxic substances by the activated leukocyte (Non Patent Document 1).

As a material having an affinity for inflammatory cytokines, the Patent Document 1 discloses a carrier for removing, in which a functional group including a urea bond and an amino group is immobilized to the surface of a water-insoluble carrier. The Patent Document 2 discloses a multifunctional carrier for removing, in which the form of carrier is fibers having a certain range of fiber diameter or the like, which enables the carrier to remove activated leukocytes in addition to inflammatory cytokines from blood.

The Patent Document 3 discloses a hollow-fiber-form blood purification membrane that can remove activated leukocytes and activated platelets.

As for a material form of a substrate, which is frequently used in addition to fibers, particles (beads) are known. The Patent Documents 4 and 5 disclose a material for removing granulocytes, activated leukocytes and activated platelets from blood by providing convexo-concave in a certain area on the surface of particles. Meanwhile, the Patent Document 6 discloses a material for producing cytokines from leukocytes by immobilizing a compound on the surface of particles having convexo-concave. Additionally, a material for removing cytokines and leukocytes by immobilizing polysaccharides on the surface of particles (Patent Document 7) or by immobilizing polyvinylpyrrolidone or the like on the surface of particles having pores (Patent Document 8), is disclosed.

PRIOR ART DOCUMENTS

Patent Documents

Patent Document 1: JP H10-147518 A
Patent Document 2: JP 2006-312804 A
Patent Document 3: JP 2011-000145 A
Patent Document 4: JP 1105-168706 A
Patent Document 5: JP 2009-254695 A
Patent Document 6: JP 2003-201251 A
Patent Document 7: JP 2014-507517 A
Patent Document 8: WO12/033522 A1

Non Patent Documents

Non Patent Document 1: J. Clin. Invest., 116, 3211-9

SUMMARY OF INVENTION

Problem to be Solved by the Invention

However, although the carrier for removing described in Patent Document 1 immobilizes functional groups on the surface of the water-insoluble carrier in order to remove inflammatory cytokines, there is no mention of a relation between the the carrier for removing and an activated leukocyte-activated platelet complex, let alone techniques for removing the complex. The inflammatory cytokine having nanometer scale-size is a protein secreted from cells, and its physical properties and bioactivities are different from those of the activated leukocyte-activated platelet complex which has micrometer scale-size and is a complex of cells. Therefore, the relation between the inflammatory cytokines and activated leukocyte-activated platelet complex has not been recognized as a target to be removed so far.

Although the carrier for removing described in Patent Document 2 specifies the physical property (zeta potential) of the carrier surface to remove a target substance to be removed, such as cytokines and leukocytes, efficiently, there is no mention of a relation between the the carrier for removing and an activated leukocyte-activated platelet complex, let alone techniques for removing the complex. Since the types of proteins being expressed on the cell surface, size of cells, and bioactivities are different between a leukocyte and an activated leukocyte-activated platelet complex, it is considered that mechanisms are not identical between the case of removing leukocyte and the case of removing the activated leukocyte-activated platelet complex.

Although the hollow-fiber-form blood purification membrane described in the Patent Document 3 specifies the center line mean roughness and ten point average roughness of the blood-contacting surface of hollow fibers to remove activated leukocytes and/or platelets, there is no mention of a relation between the hollow-fiber-form blood purification membrane and an activated leukocyte-activated platelet complex, let alone techniques for removing the complex. Since the types of proteins being expressed on the cell surface, size of cells, and bioactivities are different between the activated leukocytes or platelets and an activated leukocyte-activated platelet complex, it is considered that mechanisms are not identical between the case of removing the activated leukocytes or platelets and the case of removing the activated leukocyte-activated platelet complex.

Although the materials described in Patent Documents 4 and 5 can remove granulocytes, activated leukocytes, and activated platelets from blood by specifying a center line mean roughness of the material surface and having convexo-concave in a certain area, there is no mention of a relation between the above material and an activated leukocyte-activated platelet complex, let alone techniques for removing the complex. Further, since the types of proteins being expressed on the cell surface, size of cells, and bioactivities are different between the granulocytes and an activated leukocyte-activated platelet complex, it is considered that mechanisms are not identical between the case of removing granulocytes and the case of removing the activated leukocyte-activated platelet complex. The Patent Documents 4 and 5 are totally silent about charge of the material surface and an extending length ratio of the material surface.

A material described in Patent Document 6 is one that evokes in vivo an activity of cytokines by immobilizing mycelia, mycelia components, peptides, nucleic acids, proteins, sugar components, lipids or the like on the surface of a water-insoluble material. These immobilizing substances are not for removing cytokines but for producing them, and there is no mention of a relation between the above material and an activated leukocyte-activated platelet complex, let alone techniques for removing the complex.

The inventions described in Patent Documents 7 and 8 relate to a material (especially beads) for removing cytokines and leukocytes, but there is no description about a form of the material surface, and there is no mention of a relation between the above material and an activated leukocyte-activated platelet complex, let alone techniques for removing the complex.

Therefore, a material that can remove the activated leukocyte-activated platelet complexes is strongly demanded.

In view of these, an objective of the present invention is to provide a material for removing an activated leukocyte-activated platelet complex, which can remove the activated leukocyte-activated platelet complex with high efficiency.

Means for Solving the Problems

As a result of intensive study to solve the problems described above, the present inventors found that the activated leukocyte-activated platelet complex can be removed with high efficiency by using a water-insoluble carrier to the surface of which carrier a compound(s) having a charged functional group(s) is(are) bound and by setting an extending length ratio of the surface to a certain range.

That is, the present invention provides the following (1) to (9):

(1) A material for removing an activated leukocyte-activated platelet complex, the material being a water-insoluble carrier to the surface of which carrier a compound(s) having a charged functional group(s) is(are) bound, wherein an extending length ratio of the surface is 4 to 7.

(2) The material for removing, according to (1), wherein a center line mean roughness of the surface is 2 to 10 μm.

(3) The material for removing, according to (1) or (2), wherein the absolute value of charge amount of the functional group(s) is 0.3 to 3.0 mmol per 1 g dry weight of the water-insoluble carrier.

(4) The material for removing, according to any one of (1) to (3), wherein the charged functional group is an amino group.

(5) The material for removing, according to any one of (1) to (4), wherein the water-insoluble carrier is in the form of fibers, and the fiber has a fiber diameter of 1 to 100 μm.

(6) The material for removing, according to any one of (1) to (5), wherein the water-insoluble carrier comprises one or more polymers selected from the group consisting of polystyrene, polysulfone, and polyethersulfone.

(7) The material for removing, according to any one of (1) to (6), wherein the material adsorbs and removes an activated leukocyte, IL-6, IL-8, or HMGB-1.

(8) A column for blood purification, the column comprising the material for removing, according to any one of (1) to (7).

(9) A column for blood purification for treating a respiratory disease, the column comprising the material for removing, according to any one of (1) to (7).

Effect of the Invention

The material for removing of the present invention can remove an activated leukocyte-activated platelet complex with high efficiency, and can exert a therapeutic effect against respiratory diseases by using the material for an extracorporeal circulation column.

MODE FOR CARRYING OUT THE INVENTION

Figure 1:
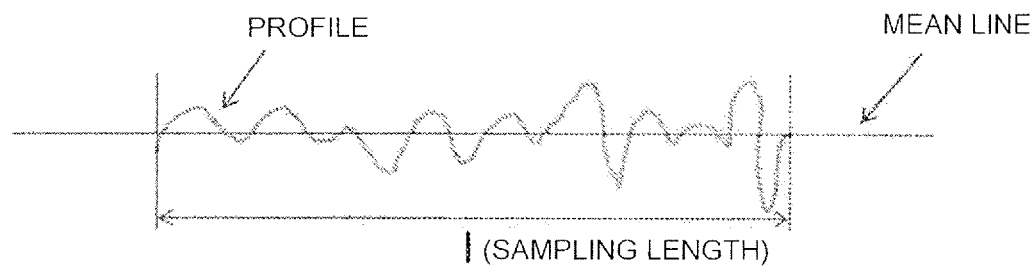
FIG. 1 is a view explaining the way of determining the extending length ratio.

The present invention will now be described in detail. It should be understood that throughout the present description, unless otherwise stated, an expression in singular form include a plural concept thereof. Therefore, it should be understood that, unless otherwise stated, the article in singular form (e.g., in English, "a", "an", "the" etc.) includes a plural concept thereof.

A material for removing an activated leukocyte-activated platelet complex of the present invention is characterized by a water-insoluble carrier to the surface of which carrier a compound(s) having a charged functional group(s) is(are) bound, wherein an extending length ratio of said surface is 4 to 7.

The "material for removing" means a material which can remove objects to be removed. The form of the material is not limited particularly, and examples thereof include the form of films, particles, and fibers. Considering the use in the treatment through extracorporeal circulation, the form of fibers, particularly the form of sea-island fibers is preferable in that it has high specific surface area and flexibly deformable nature to excel in usability. Also considering the homogeneity of packing of the material for removing and flow pass of liquid when used, the form of woven fabrics, non-woven fabrics or knitted fabrics is preferable among the forms of fibers. The material for removing an activated leukocyte-activated platelet complex may be any ones that include, at least in part, a water-insoluble carrier, and the material may be a water-insoluble carrier alone or may be one in which a suitable reinforcing material is immobilized or mixed to the water-insoluble carrier. The operation of the immobilizing or mixing may be carried out before or after the material is processed into the form. Examples of the removing method includes a method in which the object to be removed is removed by adsorption or filtration.

In cases where the water-insoluble carrier is in the form of fibers, the fiber has preferably a fiber diameter of not less than 1 μm, in the light of ensuring a flow pass in which blood cells can pass, more preferably not less than 3 μm, still more preferably not less than 5 μm, still more preferably not less than 10 μm, still more preferably not less than 15 μm. In the light of ensuring a specific surface area for adsorption, the fiber has preferably a fiber diameter of 100 μm or less, more preferably 50 µm or less, still more preferably 30 µm or less. That is, a fiber diameter of the fiber is preferably 1 to 100 µm, more preferably 3 to 100 µm, still more preferably 5 to 100 µm, still more preferably 10 to 100 µm, still more preferably 15 to 100 µm, still more preferably 15 to 50 µm, still more preferably 15 to 30 µm. Any preferable lower limit can be combined with any preferable upper limit.

The "fiber diameter" refers to an average of values that are obtained by collecting randomly 10 small piece samples of fibers forming the woven fabrics, non-woven fabrics or knitted fabrics by which the water-insoluble carrier is constituted, capturing images of each sample using a scanning electron microscope, and measuring the diameter of the fiber at 10 points per image (100 points in total). The observation magnification at this time is set to the magnification in which the fiber diameter is displayed in the range of 30 to 80% of the length of the long side of the image. In cases where the fiber is in the form of multifilaments that are bundles of a plurality of fibers, the diameter of single yarn constituting the multifilaments is used as the fiber diameter.

The "water-insoluble carrier" means to a carrier that is insoluble in water. Being insoluble in water herein means that the change of dry weight of the water-insoluble carrier between before and after the carrier is put in water is 1% by weight or less. The dry weight change is a ratio of the dry weight of remained solid contents with respect to the dry weight of a water-insoluble carrier before immersed in water, which dry weight of remained solid contents is obtained by immersing the water-insoluble carrier, for one hour, in 37° C. water whose amount is nine times larger than the dry weight of the water-insoluble carrier, then pulling the carrier out using tweezers or the like, and drying in vacuum water contained in the water-insoluble carrier at 50° C. or less to constant mass. A carrier that is not insolubilized to water has a risk of increasing the amount of eluate from the carrier when actually used, which is not preferable from a safety point of view.

Examples of a material for the water-insoluble carrier include a polymer material having, in the repeating structures, a functional group reactive with a carbocation, such as an aryl group or a hydroxyl group, e.g., synthetic polymers, such as poly(aromatic vinyl compound), polyester, polysulfone, polyethersulfone, polystyrene, or polyvinyl alcohol; or naturally-occurring polymers, such as cellulose, collagen, chitin, chitosan, or dextran. These polymers may be used as homopolymer or copolymer, or may be blended or as alloyed for use. In particular for blood purification, the material preferably includes one or more polymers selected from the group consisting of poly(aromatic vinyl compound), polyethylene terephthalate, polybutylene terephthalate, polystyrene, polysulfone, and polyethersulfone, which are polymer materials without hydroxyl groups, more preferably one or more polymers selected from the group consisting of polystyrene, polysulfone, and polyethersulfone. Among them, the material including polystyrene is particularly preferable because it has a large number of aromatic rings per unit weight, and various functional groups or reactive functional groups are introduced easily through Friedel-Crafts reaction or the like. In particular, in the case of sea-island fibers, sea components contacting the objects to be removed preferably include polystyrene. The polymer materials used for these water-insoluble carriers can be purchased commonly or can be produced by a known method.

The "compound(s) having a charged functional group(s)" means a compound(s) having a functional group(s) having a positive charge(s) or negative charge(s) and is(are) not limited particularly as long as the compound(s) can interact with the activated leukocyte-activated platelet complex. Examples of its chemical structure include a compound having an amino group which is a functional group with a positive charge (cationic functional group), or a compound having a sulfonic group or carboxyl group which is a functional group with a negative charge (anionic functional group). As the charged functional group, an amino group is preferred, and as the compound(s) having the charged functional group(s), a compound(s) including an amino group(s) is(are) preferred. The functional group may be used by combining a plurality of the same or different functional groups. The compound(s) having the charged functional group(s) may further include an uncharged functional group(s) as long as it includes the foregoing charged functional group(s). For example, the compound in which an alkyl group such as methyl or ethyl, or an aryl group such as phenyl group, a phenyl group substituted by alkyl (e.g., para(p)-methylphenyl, meta(m)-methylphenyl, ortho(o)-methylphenyl, para(p)-ethylphenyl, meta(m)-ethylphenyl, or ortho(o)-ethylphenyl), or a phenyl group substituted by a halogen atom (e.g., para(p)-fluorophenyl, meta(m)-fluorophenyl, ortho(o)-fluorophenyl, para(p)-chlorophenyl, meta (m)-chlorophenyl, or ortho(o)-chlorophenyl) is bound to the compound having the charged functional group (e.g., tetraethylenepentamine to which para(p)-chlorophenyl is bound), is included in the compound having the charged functional group(s). In this case, the uncharged functional group and the compound having the charged functional group(s) may be bonded directly, or may be bonded via a spacer (a spacer involved in such a bonding is also referred to as a spacer 1). Examples of the spacer 1 include urea bonds, amide bonds, and urethane bonds.

It is considered that as for an absolute value of the charge amount of the charged functional group, if it is too low, a sufficient interaction with substances to be removed cannot be attained, whereas if it is too much, the degree of freedom of configuration of the functional group reduces and an adequate interaction with substances to be removed cannot be attained. Thus, the absolute value is preferably 0.3 to 3.0 mmol per 1 g of dry weight of the water-insoluble carrier, more preferably 0.4 to 2.9 mmol, still more preferably 0.5 to 2.7 mmol. Any preferable lower limit can be combined with any preferable upper limit.

Examples of the "amino group" include amino groups derived from primary amines, such as methylamine, ethylamine, propylamine, butylamine, pentylamine, hexylamine, heptylamine, octylamine, or dodecylamine; amino groups derived from secondary amines, such as methylhexylamine, diphenylmethylamine, dimethylamine; amino groups derived from amines having unsaturated alkyl chain, such as allylamine; amino groups derived from tertiary amines, such as trimethylamine, triethylamine, dimethylethylamine, phenyldimethylamine, dimethylhexylamine; amino groups derived from amines having aromatic rings, such as 1-(3-aminopropyl)imidazole, pyridin-2-amine, 3-sulfoaniline; or amino groups derived from compounds in which two or more amino groups are bonded to alkyl chains, aromatic compounds, heterocyclic compounds, homocyclic compounds or the like (hereinafter, "polyamine"), such as tris (2-aminoethyl)amine, ethylendiamine, diethylenetriamine, triethylenetetramine, tetraethylenepentamine, dipropylenetriamine, polyethyleneimine, N-methyl-2,2'-diaminodiethylamine, N-acetyl-ethylenediamine, 1,2-bis(2-aminoethoxyethane). The amino group is preferably amino groups derived from polyamine, in particular, preferably amino groups derived from ethylendiamine, diethylenetriamine, triethylenetetramine, or tetraethylenepentamine, more preferably, amino groups derived from tetraethylenepentamine. In addition, the amino group is more preferably amino groups derived from primary amines or secondary amines.

The compound including a sulfonic group may be any one as long as it has at least one sulfonic group, and examples of the sulfonic group include a sulfonic acid group derived from aliphatic sulfonic acids, such as sulfonic acid, methanesulfonic acid; a sulfonic acid group derived from aromatic sulfonic acids, such as benzenesulfonic acid, p-phenolsulfonic acid, 4-methylbenzenesulfonic acid; or, a sulfonic acid group derived from halosulfonic acids, such as fluorosulfonic acid, and chlorosulfonic acid.

The compound including a carboxyl group may be any one as long as it has at least one carboxyl group, and examples of the carboxyl group include a carboxyl group derived from aliphatic carboxyl groups, such as acetic acid, and propionic acid; or a carboxyl group derived from aromatic carboxyl groups, such as benzenecarboxyl group.

The water-insoluble carrier and the compound having the charged functional group(s) may be bound directly, or may be bound through a spacer derived from reactive functional groups between the water-insoluble carrier and the compound having the charged functional group(s) (a spacer involved in such a bonding is also referred to as a spacer 2). The spacer 2 may be any ones that have an electrically-neutral chemical bond, such as urea bonds, amide bonds, ether bonds, ester bonds, or urethane bonds, and preferably one having amide bonds or urea bonds.

Examples of the reactive functional groups mediating the bonding between the water-insoluble carrier and the compound having the charged functional group(s) include activated halogen groups, such as halomethyl groups, haloacetyl groups, haloacetamidemethyl groups, or alkyl halide groups; epoxide groups, carboxyl groups, isocyanic acid groups, thio-isocyanic acid groups, or acid anhydride groups. In the light of having a proper reactivity, the reactive functional group is preferably activated halogen group, more preferably haloacetamidemethyl group. Specific examples of polymer materials to which the reactive functional group is introduced include a polystyrene added with a chloroacetamidemethyl group; and polysulfone added with a chloroacetamidemethyl group.

The reactive functional group can be bound to the water-insoluble carrier by reacting with the water-insoluble carrier and a suitable reagent in advance. For example, in cases where the water-insoluble carrier is polystyrene and the reactive functional group is a chloroacetamidemethyl group, the polystyrene and N-methylol-α-chloroacetamide can be reacted to obtain a polystyrene to which chloroacetamidemethyl group is bound. To the polystyrene to which chloroacetamidemethyl group is bound, for example, tetraethylenepentamine having an amino group is reacted, thereby obtaining a polystyrene to which tetraethylenepentamine is bound through an acetamidemethyl group. In this case, the acetamidemethyl group corresponds to the spacer 2, and the tetraethylenepentamine corresponds to the compound having the charged functional group(s). Materials of the water-insoluble carrier, the spacers (spacer 1 and spacer 2), and the compound having the charged functional group(s) can be optionally combined. Examples of the water-insoluble carrier to the surface of which carrier a compound(s) having a charged functional group(s) is(are) bound include a polystyrene to which a compound including amino groups derived from ethylenediamine, diethylenetriamine, triethylenetetramine, or tetraethylenepentamine is bound through an acetamidemethyl group; a polysulfone to which a compound including amino groups derived from ethylenediamine, diethylenetriamine, triethylenetetramine, or tetraethylenepentamine is bound through an acetamidemethyl group; and a polyethersulfone to which a compound including amino groups derived from ethylenediamine, diethylenetriamine, triethylenetetramine, or tetraethylenepentamine is bound through an acetamidemethyl group. Starting materials and reagents used for producing the material for removing an activated leukocyte-activated platelet complex can be purchased commonly, or can be produced by a known method.

Since the compound having the charged functional group(s) is required to interact with substances to be removed in blood, the compound is required to be bound to at least a side which comes into contact with blood, of surfaces of the water-insoluble carrier. In the case of sea-island fibers, the compound having the charged functional group(s) is required to be bound to at least a surface which comes into contact with blood, of the sea components. The surface herein means a surface of the water-insoluble carrier, and when the surface of the water-insoluble carrier has the form having convexo-concave, the most outer layer portion along the convexo-concave is included in the surface in addition to the surface of the water-insoluble carrier. Further, when the inside of the water-insoluble carrier has through-holes, the surface includes not only the most outer layer portion of the water-insoluble carrier but also outer layers of the through-holes inside the water-insoluble carrier.

The "extending length ratio (Rlr)" refers to a ratio of an extending length (Rlo (μm)) and a sampling length (l (μm)). Specifically, using an analysis feature for line roughness (e.g., Shape Analysis Application VK-H1A1/VK-H2A1, manufactured by KEYENCE Corp.) and using a laser microscope (e.g., Ultra-Depth Color 3D Dimensional Measurement Microscope VK-9710, manufactured by KEYENCE Corp.), images of a material surface to be measured are captured, the extending length (Rlo) is calculated from the obtained image, and the ratio of the resultant extending length (Rlo) and a sampling length (l) that is drew from a profile to its mean line direction is calculated. As shown in FIG. 1, the extending length (Rlo) is a value that indicates a true length of an extracted part that is obtained by extracting the profile by the sampling length (l) in its mean line direction. Therefore, the extending length (Rlo) represents a length of cases where the convexo-concave of the profile of the material surface is stretched into a straight line. Further, the extending length ratio is calculated from the following Equation 1, where Rlo represents an extending length, Rlr represents an extending length ratio, and l represents a sampling length. Such operations are performed in any nine fields of view to calculate an average value of them, thereby obtaining the extending length ratio.

Although the detailed mechanism is unknown, in the case of removing the activated leukocyte-activated platelet complex, if the extending length ratio of the surface of the water-insoluble carrier is too low, the area that can be used for the removing becomes narrow. Thus, the extending length ratio is required to be not less than 4. On the other hand, if the extending length ratio of the surface of the water-insoluble carrier is too high, the surface area becomes wider, but the surface has a folded structure. Thus, cells cannot enter into such a surface and the area to which the cells can actually attach becomes smaller. Therefore, the extending length ratio is required to be seven or less. That is, it is necessary that the extending length ratio of the surface of the water-insoluble carrier is 4 to 7. The extending length ratio of the surface of the water-insoluble carrier is preferably 4.2 to 6.5, more preferably 4.2 to 6. Any preferable lower limit can be combined with any preferable upper limit.

$$Rlr = Rlo/l \qquad \text{Equation 1}$$

Figure 2:
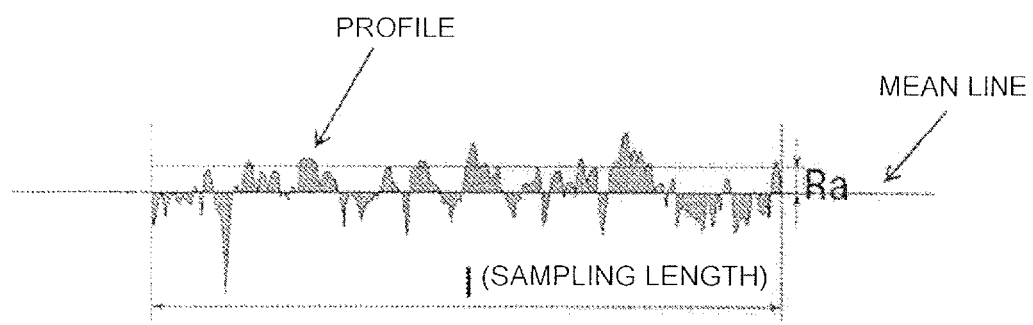
FIG. 2 is a view explaining the way of the center line mean roughness.

The "center line mean roughness (Ra (μm))" means an index for quantitating smoothness of surface, which is standardized in JIS B 0601: 2001, and refers to convexo-concaveness state of a material surface that comes into contact with blood components. Specifically, using an analysis feature for line roughness (e.g., Shape Analysis Application VK-H1A1/VK-H2A1, manufactured by KEYENCE Corp.) and using a laser microscope (e.g., Ultra-Depth Color 3D Dimensional Measurement Microscope VK-9710, manufactured by KEYENCE Corp.), images of a material surface to be measured are captured, the center line mean roughness can be calculated from the obtained image. As shown in FIG. 2, the center line mean roughness is a value that is obtained by extracting the profile by the sampling length l (μm) in its mean line direction, then adding up absolute values (μm) of deviations from the mean line to the measured curve of the extracted portions, and averaging the obtained values. The calculation method is as shown in Equation 2 below, where Ra represents a center line mean roughness, and f(x) represents a function representing surface convexo-concave shape at any position x in the laser microscope image.

$$Ra = \frac{1}{l} \int_0^l |f(x)| dx \qquad \text{Equation 2}$$

The center line mean roughness of the surface of the water-insoluble carrier is preferably 2 to 10 μm, more preferably 2.1 to 7 μm, more preferably 2.2 to 6 μm, still more preferably 2.2 to 3.5 μm. Any preferable lower limit can be combined with any preferable upper limit.

Figure 3:
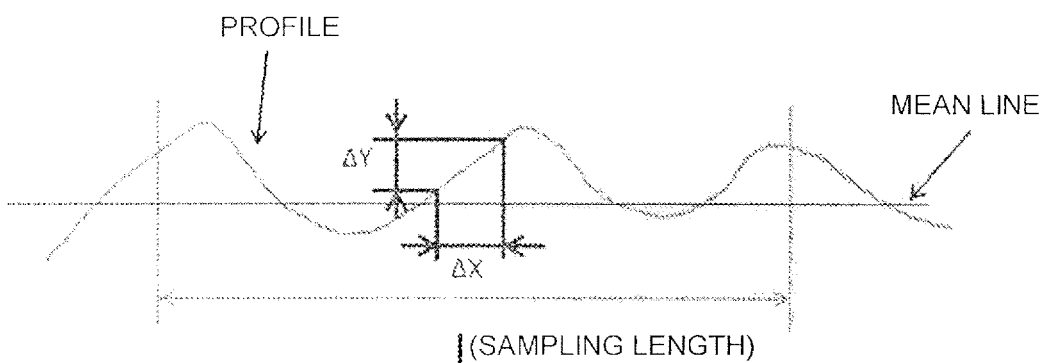
FIG. 3 is a view explaining the way of determining the root mean square slope angle.

The "root mean square slope angle (°)" indicates to a slope angle of a peak in a sampling length (l) of the material. Specifically, the root mean square slope angle is a value obtained by capturing, using an analysis feature for line roughness (e.g., Shape Analysis Application VK-H1A1/VK-H2A1, manufactured by KEYENCE Corp.) and using a laser microscope (e.g., Ultra-Depth Color 3D Dimensional Measurement Microscope VK-9710, manufactured by KEYENCE Corp.), images of a material surface to be measured, dividing the profile by a certain interval Δx in a horizontal direction from the obtained image as shown in FIG. 3, and then determining a mean square of a slope (angle) of a segment that links the end and initial points of the profile in each of the intervals to represent a square root of the obtained value. This analysis obtains values that are obtained by applying mean square to angles made by a line linking two adjoining points and a parallel line, across all the intervals. The root mean square slope angle is calculated from the following Equation 3.

$$\text{Root Mean Square Slope Angle} = \sqrt{\frac{1}{N-1} \sum_{n=0}^{N-1} \left\{ \tan^{-1}\left(\frac{\Delta Y_n}{\Delta X}\right) \right\}^2} \qquad \text{Equation 3}$$

The root mean square slope angle in Equation 3 is occasionally abbreviated as RΔq.

In the case of removing the activated leukocyte-activated platelet complex, if the root mean square slope angle of the surface of the water-insoluble carrier is too small, the adhesive property between the materials and cells becomes low. Thus, the root mean square slope angle is required to be not less than 50°. Further, if the root mean square slope angle of the surface of the water-insoluble carrier is too large, the frequencies for the cells to recognize the materials become high, but since a local portion thereof has a steep structure, the adhesive property of cells to the materials becomes weaker. Thus, the slope angle is required to be 85° or less. That is, it is necessary that the root mean square slope angle of the surface of the water-insoluble carrier is 50 to 85°, more preferably 65 to 75°. Any preferable lower limit can be combined with any preferable upper limit. The preferable ranges of the foregoing extending length ratio, center line mean roughness and root mean square slope angle can be optionally combined. For example, the extending length ratio of the surface of the water-insoluble carrier is 4 to 7, and the center line mean roughness of the surface of the water-insoluble carrier is 2.1 to 7 μm.

Figure 4:
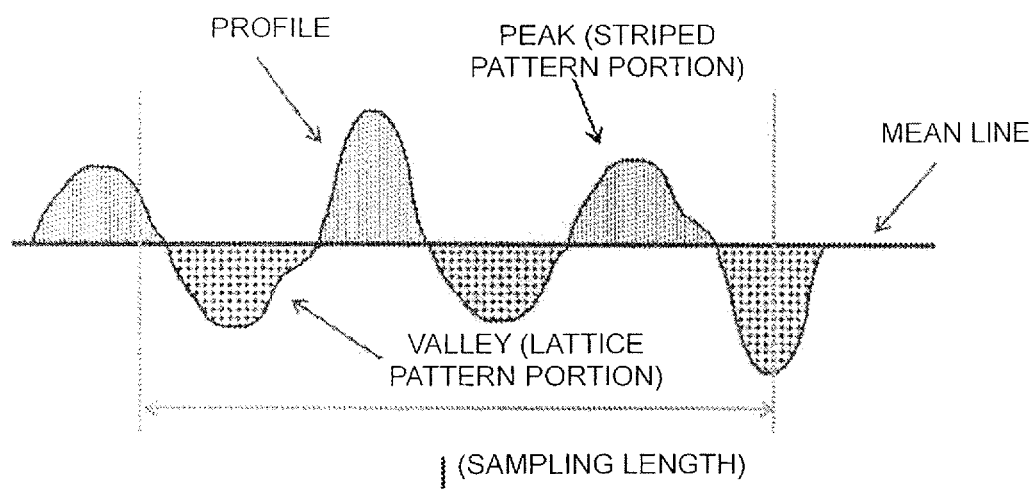
FIG. 4 is a view explaining the way of analyzing the line roughness.

The profile means a curved line, as shown in FIG. 4, obtained by following the contour of the material surface at the moment of capturing images of the surface of the material to be measured with the laser microscope, and in the present application, refers to a measured sectional curve of the material. The profile is a curved line different from a sectional curve obtained by applying a phase compensation-type low-pass filter whose cutoff value is λs to the measured sectional curve; a roughness curve obtained by recording only high-frequency components in the sectional curve through a phase compensation-type high-pass filter (cutoff value λc); and, a waviness curve obtained by applying a phase compensation-type filter whose cutoff values are λf and λc to the sectional curve.

The mean line refers to a line in which the profile is converted to a straight line by least-squares method, as defined in JIS B 0601: 1994. The peak refers to each of portions that are above the mean line, and are portions with striped pattern in FIG. 4. The valley refers to each of portions that are below the mean line, and are portions with lattice pattern in FIG. 4. The sampling length is obtained from a portion that is extracted by a certain length from the profile, and refers to such a length to be extracted.

Since measured values of the foregoing extending length ratio, center line mean roughness, and root mean square slope angle may vary in accordance with conditions for capturing images of the laser microscope, the conditions for capturing images are set as described below. The material is put on a slide glass such that the material is wet with distilled water and the surface that comes into contact with blood can be observed, and the material is covered with a cover glass (thickness: 0.12 to 0.17 mm) from above. In this case, the material is set between the cover glass and the slide glass so as to be the thickness of the material to 50 μm or less. For example, in cases where the material is fibers, beads or hollow fibers, if the diameter of the fibers, diameter of the beads or outer diameter of the hollow fibers is not less than 50 μm, the material is sliced into 50 μm or less such that the surface that comes into contact with blood can be observed. Especially in the case of the hollow fibers, the material is sliced such that the surface that comes into contact with blood can be observed. Additionally, the material is inserted between the cover glass and the slide glass such that both of them is parallel each other, and excess distilled water overflowed from the cover glass is removed to fill water evenly in the space therebetween. The images are captured from above the cover glass. The objective lens magnification is set to 20 times, an optical zoom is set to one time, and a neutral filter is not used. Since the extending length ratio, the center line mean roughness, and the root mean square slope angle may vary in accordance with analysis conditions, the analysis conditions are set as described below. For analysis, a line roughness analysis is used and a sampling length l is 50 μm, and the image analysis is performed with no waviness corrections and no settings for cutoff values of filters. Images at three positions are captured randomly per one material, and the image analysis is performed to three fields of view for each captured image, thus performing the image analysis for total nine fields of view. Surface roughness for each field of view is calculated, and the average value of them is employed as the surface roughness of the material. In the case of fibers or hollow fibers, as the sampling length at the time of the image analysis, a portion in which the fiber is parallel to the longitudinal direction of the fibers and whose surface is even in height is selected.

The configurations of the material surface (extending length ratio, center line mean roughness, and root mean square slope angle) can be regulated by production conditions of the water-insoluble carrier, e.g. concentration of paraformaldehyde and reaction time when producing a chloroacetamidemethylated knitted fabric. In introducing the chloroacetamidemethyl group into the water-insoluble carrier, as dissolution of the material surface proceeds, the extending length ratio tends to be longer, the center line mean roughness tends to be higher, and the root mean square slope angle tends to be larger. In this case, since as the concentration of paraformaldehyde to be added increases, cross-linking of the water-insoluble carrier is promoted to inhibit dissolution of the surface of the carrier, the extending length ratio tends to be shorter, the center line mean roughness tends to be lower, and the root mean square slope angle tends to be smaller. In cases where the concentration of paraformaldehyde to be added is constant and the degree of cross-linking is constant, as the reaction time when introducing the chloroacetamidemethyl group into the water-insoluble carrier becomes longer, the extending length ratio tends to be longer, the center line mean roughness tends to be higher, and the root mean square slope angle tends to be larger, because the dissolution of the surface of the carrier is promoted. For example, as for the the water-insoluble carrier described in the Patent Document 2, the concentration of paraformaldehyde when producing a chloroacetamidemethylated knitted fabric is 0.2 wt % which is lower than that of Example 7. Thus, it is considered that the extending length ratio and center line mean roughness are greater than those of Example 7.

The configurations of the material surface (extending length ratio, center line mean roughness, and root mean square slope angle) can be further regulated by the concentration of tetraethylenepentamine and reaction time when producing a tetraethylenepentamine-p-chlorophenylated knitted fabric. In introducing the tetraethylenepentamine into the water-insoluble carrier, as the concentration of tetraethylenepentamine to be added increases, swelling of the material surface proceeds, the extending length ratio tends to be shorter, the center line mean roughness tends to be higher, and the root mean square slope angle tends to be larger. Further, since as the reaction time when introducing the tetraethylenepentamine into the water-insoluble carrier increases, the swelling of the material surface is promoted, the extending length ratio tends to be shorter, the center line mean roughness tends to be higher, and the root mean square slope angle tends to be larger.

The charge amount of the charged functional group can be measured by an acid-base titration using hydrochloric acid or aqueous sodium hydroxide.

The "blood" refers to a liquid including proteins, lipids, blood cell components and the like. Specifically, the liquid includes one in which proteins, lipids, blood cell components and the like are added in buffer; body fluid, blood, plasma or serum. The blood component refers to a component constituting blood, and examples thereof include blood cell components such as erythrocytes, leucocytes or platelets, or humoral factors such as cytokines. In the case of purpose to treat inflammatory diseases, among the components above, leucocytes (especially, activated leukocytes) or cytokines (especially, inflammatory cytokines such as interleukin-6, interleukin-8, high-mobility group protein-1) are preferably removed.

The "leucocytes" refer to immunocyte components contained in blood, and specifically the examples thereof include a granulocyte, monocyte and lymphocyte, and also include an activated granulocyte, activated monocyte and activated lymphocyte which are the activated components thereof.

The "cytokines" refer to proteins that are secreted by cells, which transfer information to specified cells, and examples thereof include interleukins, tumor necrosis factor-α, transforming growth factor-β (hereinafter, TGF-β), interferon-γ (hereinafter, INF-γ), high-mobility group protein-1 (hereinafter, HMGB-1), angiogenic growth factor, and/or immunosuppressive acidic protein. Among them, a cytokine that is involved in inflammation is referred to as an inflammatory cytokine, and in the case of purpose to treat inflammatory diseases, these inflammatory cytokines of the interleukin and/or HMGB-1 are preferably removed.

The "interleukins" refer to cytokines that are secreted by leucocytes, which function in regulation of immune system, and examples thereof include interleukin-1 (hereinafter, IL-1), interleukin-6 (hereinafter, IL-6), interleukin-8 (hereinafter, IL-8), interleukin-10 (hereinafter, IL-10), interleukin-17 (hereinafter, IL-17). In the case of purpose to treat inflammatory diseases, IL-6 and/or IL-8 are preferably removed.

The "activated leukocytes" mean leukocytes to release inflammatory cytokines, active oxygen or the like by cytokine, lipopolysaccharide (LPS) which is endotoxin, or the like, and examples thereof include activated granulocytes and activated monocytes. The degree of activation can be determined by measuring the amount of activated oxygen released by activated leukocytes or measuring the expression of surface antigens by flow cytometry or the like.

The "activated platelets" mean platelets to release inflammatory cytokines, active oxygen or the like by cytokines, lipopolysaccharide (LPS) which is endotoxin, or the like.

The "activated leukocyte-activated platelet complexes" are not limited particularly as long as they are complexes in which an activated leukocyte and an activated platelet are bound, and examples thereof include activated granulocyte-activated platelet complexes and activated monocyte-activated platelet complexes. For patients with an inflammatory disease, especially for patients with a respiratory disease, it is thought that the activated leukocyte-activated platelet complexes are directly involved in the pathology through phagocytosis into self-tissues and release of inflammatory cytokines, and it is considered that removing the activated leukocyte-activated platelet complexes is required for treating the disease.

The "inflammatory disease" may be an inflammatory disease that can be diagnosed in medical field, and is not limited to a particular one. Specifically, examples thereof include acute lung injury (ALI), acute respiratory distress syndrome (ARDS), pneumonia, acute respiratory failure, systemic inflammatory syndrome, septicemia, septic shock, toxic shock syndrome, multiple organ failure, chronic obstructive pulmonary disease, cachexia, infection, parasitic disease, rheumatoid arthritis, osteoarthritis, juvenile chronic arthritis, Lyme arthritis, psoriatic arthritis, reactivation arthritis, spondylarthropathy, systemic lupus erythematosus, Crohn's disease, colitis ulcerosa, inflammatory bowel disease, insulin-dependent diabetes mellitus, thyroiditis, asthma, allergic disease, psoriasis, scleroderma dermatitis, graft versus host disease, organ transplant rejection, acute or chronic immune disease accompanied with organ transplant, sarcoidosis, atherosclerosis, disseminated intravascular coagulation syndrome, Kawasaki disease, Graves disease, nephrotic syndrome, chronic fatigue syndrome, Wegener's granulomatosis, anaphylactoid purpura, microscopic vasculitis of the kidneys, chronic active hepatitis, uveitis, acquired immunodeficiency syndrome, acute transverse myelitis, Huntington's chorea, Parkinson's disease, Alzheimer's disease, attack, primary biliary cirrhosis, hemolytic anemia, malignant disease, cardiac failure, cardiac infarction, Addison's disease, sporadic disease, type I multi secretory gland hypofunction and type II multi secretory gland hypofunction, Schmidt's syndrome, alopecia, alopecia areata, seronegative arthropathy, arthropathy, Reiter's disease, psoriatic arthropathy, ulcerative arthropathy of condyle, intestinal synovitis, *Chlamydia, Yersinia* and *Salmonella*-associated arthropathy, spondyloarthropathy, atheroma disease/arteriosclerosis, atopy, autoimmune bullous disease, pemphigus vulgaris, pemphigus foliaceus, pemphigoid, IgA disease, autoimmune hemolytic anemia, Kuhn-positive hemolytic anemia, acquired pernicious anemia, juvenile pernicious anemia, myalgic encephalitis/Royalfree Disease, chronic mucocutaneous candidiasis, giant cell arteritis, acute hepatitis, primary sclerotic hepatitis, cryptogenic autoimmune hepatitis, acquired immunodeficiency disease syndrome, acquired immunodeficient-associated disease, hepatitis C, unclassifiable immunodeficiency (unclassifiable hypogammaglobulinemia), dilated cardiomyopathy, female sterility, ovarian failure, premature ovarian failure, idiopathic pulmonary fibrosis, fibrotic pulmonary disease, cryptogenic fibrosing alveolitis, post inflammatory interstitial lung disease, spatia pneumonia, interstitial lung disease accompanied with connective-tissue disease, lung disease accompanied with mixed connective-tissue disease, interstitial lung disease accompanied with systemic sclerosis, interstitial lung disease accompanied with rheumatoid arthritis, lung disease accompanied with systemic lupus erythematosus, lung disease accompanied with dermatomyositis/polymyositis, lung disease accompanied with Sjogren's disease, lung disease accompanied with ankylosing spondylitis, vascular diffuse lung disease, lung disease accompanied with hemosiderosis, drug-induced interstitial lung disease, radiation fibrosis, bronchiolitis obliterans, chronic eosinophilic pneumonia, lymphocytic-infiltrating lung disease, postinfection interstitial lung disease, urarthritis, autoimmune hepatitis, type 1 autoimmune hepatitis (classical autoimmune or lupoid hepatitis), type 2 autoimmune hepatitis (anti-LKM antibody hepatitis), autoimmune-mediated hypoglycemia, type B insulin resistance accompanied with acanthosis nigricans, hypoparathyroidism, acute immune disease accompanied with organ transplant, chronic immune disease accompanied with organ transplant, steoarthrosis, primary sclerosing cholangitis, type 1 psoriasis, type 2 psoriasis, idiopathic leukopenia, autoimmune neutropenia, renal disease NOS, glomerulonephritis, microscopic angiitis of the kidneys, Lyme disease, discoid lupus erythematosus, agnogenic or NOS male sterility, sperm autoimmunization, disseminated sclerosis (all subtypes), sympathetic ophthalmia, auxiliary esmosis pulmonary hypertension of connective tissue disease, Goodpasture's syndrome, lung expression of polyarteritis nodosa, acute rheumatism, rheumatoid spondylitis, Still's disease, systemic sclerosis, Sjogren's syndrome, Takayasu's disease/arteritis, autoimmune thrombocytopenia, idiopathic thrombocytopenia, autoimmune thyroid disease, hyperthyroidism, goiter autoimmune hyperthyroidism (Hashimoto's disease), atrophic autoimmune hypothyroidism, primary myxedema, phacogenic uveitis, primary angiitis, or vitiligo.

The "respiratory disease" may be any respiratory disease that can be diagnosed in medical field, and is not limited to a particular one. Specifically, examples thereof include acute lung injury (ALI), acute respiratory distress syndrome (ARDS), pneumonia, acute respiratory failure, chronic obstructive pulmonary disease, idiopathic pulmonary fibrosis, fibrotic pulmonary disease, cryptogenic fibrosing alveolitis, post inflammatory interstitial lung disease, interstitial pneumonia, interstitial lung disease accompanied with connective-tissue disease, lung disease accompanied with mixed connective-tissue disease, interstitial lung disease accompanied with systemic sclerosis, interstitial lung disease accompanied with rheumatoid arthritis, lung disease accompanied with systemic lupus erythematosus, lung disease accompanied with dermatomyositis/polymyositis, lung disease accompanied with Sjogren's disease, lung disease accompanied with ankylosing spondylitis, vascular diffuse lung disease, lung disease accompanied with hemosiderosis, drug-induced interstitial lung disease, radiation fibrosis, bronchiolitis obliterans, chronic eosinophilic pneumonia, lymphocytic-infiltrating lung disease, postinfection interstitial lung disease or the like. The foregoing material for removing the activated leukocyte-activated platelet complex is preferably used to treat acute lung injury (ALI), acute respiratory distress syndrome (ARDS) among the respiratory diseases.

The concentration of the activated leukocyte-activated platelet complex can be measured, for example, in such a manner that an activation detection reagent that binds specifically to an activated platelet (an activated platelet binding reagent) and an activation detection reagent that binds specifically to an activated leukocyte (an activated leukocyte detection reagent/an activated granulocyte detection reagent/an activated monocyte detection reagent) are reacted with the fraction of leukocytes derived from peripheral blood, and then the fraction of the blood cells bound to both the reagents is measured.

The activated platelet detection reagent does not bind to a deactivated leukocyte nor an activated leukocyte, and has the binding ability with an activated platelet, and the activated platelet is detected using CD62P (Anti-human CD62P (P-Selectin) Antibody Data Sheet, BioLegend.) known as a cell surface marker specific to an activated platelet. The activated leukocyte detection reagent does not bind to a deactivated platelet nor an activated platelet and has the binding ability with an activated leukocyte, and examples thereof include an antibody specific to a desired leukocyte component or an antibody against a cell surface marker common to a desired leukocyte component. As a detection reagent for an activated granulocyte and activated monocyte, for example, an anti-CD11b antibody can be used.

Among these, by using an activated anti-CD11b antibody that can specifically detect an activated conformation, the activated granulocyte and activated monocyte can be detected specifically (Anti-human CD11b (activated) Antibody Data Sheet, BioLegend.). An anti-CD45 antibody can be used to detect leukocytes, an anti-CD66b antibody in a CD45 positive cell can be used to detect granulocytes, and an anti-CD14 antibody in a CD45 positive cell can be used to detect monocytes. To detect lymphocytes, an anti-CD4 antibody and an anti-CD8 antibody can be used, and it is also possible that a cell population obtained by subtracting CD66b positive cells and CD14 positive cells from CD45 positive cells is regarded as lymphocytes.

The foregoing detection reagents preferably have an index for verifying the binding. Any index can be selected in accordance with an adopted detection method. A flow cytometer is used for measurement in view of easy operation or quantitativeness, in which case the detection reagent is fluorescently-labeled. The fluorescent label is not limited to a particular one, and, for example, labeling with a FITC (fluorescein isothiocyanate) or an PE (R-phycoerythrin) can be adopted. The activated leukocyte detection reagent and the activated platelet detection reagent are labeled with different fluorescent substances. These labeled detection reagents can be produced by a conventional method, and is also commercially available.

The reaction between the leukocyte fraction and the foregoing detection reagent is suitably set in accordance with the detection reagent adopted. When the detection reagent is an antibody, the reaction has only to be subjected to a usual immunoreaction. The activated leukocyte-activated platelet complex and the detection reagent reaction liquid are not limited to particular ones, and, if desired, may contain sodium azide or formaldehyde in an amount effective in inhibiting the activation of cell components during detection reaction. The reaction temperature is not limited particularly, and is preferably about 4° C. in view of inhibiting the activation of cell components.

For an inflammatory disease such as a respiratory disease, it is preferable to remove the activated leukocytes and inflammatory cytokines that are involved in acute and chronic inflammations, especially the activated leukocytes, IL-6, IL-8, or HMGB-1, in addition to removal of the activated leukocyte-activated platelet complex. The inflammatory cytokines are generally a protein having about a few thousands to tens of thousands of molecular weight, and in the inflammatory cytokines, there are a hydrophobic moiety and an electrification moiety. Since it is therefore considered that removing through hydrophobic interaction or electrostatic interaction is effective for removal of the inflammatory cytokines, it is preferred that one or both of the hydrophobic functional group or charged functional group be present in the surface of the water-insoluble carrier. Specifically, the hydrophobic functional group is preferably alkyl such as methyl or ethyl; or aryl such as phenyl; and the charged functional group is preferably amino, sulfonic, or carboxyl groups, but is not limited thereto.

Examples of methods of calculating a removal rate of an activated granulocyte, an activated monocyte, an activated granulocyte-activated platelet complex, and an activated monocyte-activated platelet complex include, for example, a method in which the material for removing are packed inside a column (container) having an inlet and outlet, a liquid including an activated granulocyte, an activated monocyte, an activated granulocyte-activated platelet complex and an activated monocyte-activated platelet complex is passed through the container, and the removal rate is calculated from the change between the concentrations thereof at the inlet and at the outlet. The material for removing an activated leukocyte-activated platelet complex herein refers to a material whose removal rate calculated from the concentration change at the inlet and outlet is a positive value. As another method, in cases where a removal rate obtained from a column (empty column) that is not packed with the material for removing inside thereof as a control for an evaluation system is considered as one to calculate the ratio of interest, the material for removing refers to a material indicating a ratio greater than one (ratio >1).

Examples of a calculating method of the removal rate of cytokines include a method in which the material for removing is added to a liquid including cytokines during a certain time, and the removal rate is calculated from the concentration change between before and after the addition of the material for removing. The material for removing cytokines described in the present application refers to a material having the removal rate of not less than 10%.

Examples of an evaluation method for inhibition of pulmonary function (P/F value) decline include a method in which, as for an ARDS onset animal model produced by intratracheal administration of hydrochloric acid (HCl) and LPS (Reference: Japan Geriatrics Society Journal, Vol. 30, 1032-1038 (1993)), the blood thereof is passed through a column (container) which has an inlet and outlet and inside of which the material for removing is packed, and extracorporeal circulation is performed to evaluate inhibitory effects from the pulmonary function (P/F value) before and after of the circulation.

The present invention provides a column for blood purification, which comprises the foregoing material for removing an activated leukocyte-activated platelet complex.

The container configuration of the column packed with the material for removing an activated leukocyte-activated platelet complex may be any configurations as long as the container has a blood inlet and blood outlet and the material for removing an activated leukocyte-activated platelet complex can be packed inside the container. One embodiment is a container inside of which a cylindrical body formed by winding the material for removing an activated leukocyte-activated platelet complex around a pipe whose side has pores into cylindrical form (hereinafter, cylinder), can be packed, and examples of the container include a container in which blood enters the cylinder from its circumference to flow into the inside of the cylinder, and then the blood is discharged from the container via the pipe; or a container in which blood enters the inside of the cylinder via the pipe to flow into the outside of the cylinder, and then the blood is discharged from the container. In view of production efficiency or inhibition of bypassing of the treated liquid, the container has preferably a structure in which the material for removing the activated leukocyte-activated platelet complex is wound around the pipe whose side has pores. Specifically, examples thereof include a radial flow type container that includes a central pipe having pores on its longitudinal side, which pores are provided to flow blood out; the material for removing an activated leukocyte-activated platelet complex which are packed around the central pipe and removes the activated leukocyte-activated platelet complex contained in the blood; a plate that is communicated with the upstream end of the central pipe such that the blood passes through the inside of the central pipe, and that is arranged so as to prevent that the liquid does not pass the central pipe to come into contact with the carrier for removing; a plate that blocks the downstream end of the central pipe, and that is arranged so as to immobilize the carrier for removing to a space around the central pipe. Examples of the shape of the container include cylinder or prism such as triangular prism, quadrangular prism, hexagonal prism or octagonal prism, but are not limited to such structures. As another embodiment, there is a container that has a cylindrical space thereinside in which material for removing the activated leukocyte-activated platelet complex, that is cut out into circular shape, can be packed, and that has a blood inlet and blood outlet. Specifically, examples thereof include a container comprising thereinside a plate that comprises a blood inlet provided to flow the supplied blood out; a plate that comprises a blood outlet provided to discharge the supplied blood; and a cylindrical space in which the material for removing the activated leukocyte-activated platelet complex, that is cut out into circular shape, is packed; which container has a blood inlet and blood outlet. In this case, the shape of the material for removing the activated leukocyte-activated platelet complex is not limited to circular shape, and can be changed properly to any other shape of oval; polygon such as triangle or rectangle, trapezoid, or the like in accordance with the container configuration of the column.

Examples of materials of the column (container) to be packed with the material for removing an activated leukocyte-activated platelet complex include glass, plastics or resin, stainless or the like. Size of the column is selected properly in accordance with intended use thereof and is not limited to a particular one. In view of operability in clinical sites or measurement locations or ease of disposal, the material is preferably made of plastics or resin and preferably has easy-to-grip size. Thus, it is preferred that the longitudinal length of the whole column be 1 to 30 cm, the external diameter be 2 to 10 cm, and the internal volume be 200 cm$^3$ or less.

The material for removing an activated leukocyte-activated platelet complex is preferably packed by stacking one another in the column (container). The stacking herein means to stack closely two or more of the materials for removing an activated leukocyte-activated platelet complex. Examples of methods for packing by stacking them include a method in which a plurality of the materials for removing an activated leukocyte-activated platelet complex, which are processed into sheet form, are stacked like an axial flow column; and a method in which the material for removing an activated leukocyte-activated platelet complex, which is processed into sheet form, is wound around the pipe whose side has pores, like a radial flow column.

The column for blood purification can be used to treat respiratory diseases of mammals (e.g., rabbit, human, sheep, monkey, horse, cow, pig, dog, cat), especially can be used suitably for treatment of acute lung injury (ALI) and acute respiratory distress syndrome (ARDS).

Further, a method of blood purification characterized by passing the blood of patients with respiratory disease through the above-described column for blood purification, is provided. In other words, a method of treating the respiratory disease of the respiratory disease patient by using the above-described column for blood purification, is provided. The method of blood purification can be provided alone, and also can be provided in combination with oxygenation therapy or renal replacement therapy.

EXAMPLES

The present invention will now be specifically described with reference to Experimental examples and Comparative examples, but the present invention is not limited to these examples. Among compounds used for production of each knitted fabric, for compounds whose synthesis methods are not described, commercially-available compounds were used. In Examples, wt % means percent by weight, and mM means number of millimoles of the component contained in a 1 L of solution (e.g., when 10 mmol of the component is contained in a 1 L of solution, it is represented as 10 mM).

(Spinning)

Using the following components and under a yarn-making condition of spinning rate of 1250 m/minute, 36 filaments of 704-island sea-island fiber per one filament (fiber diameter: 3 dtex, 20 μm) were bundled to obtain a fiber.

Island component: polypropylene
Sea component: polystyrene
Composite ratio (weight ratio): Island:Sea=50:50

(Producing of Knitted Fabric)

The obtained fiber was used to produce a knitted fabric by weft knitting. Using a tube knitting machine (machine name: Circular knitting machine MR-1, Maruzen Sangyo Co., Ltd.), the knitted fabric was produced.

(Production of Chloroacetamidemethylated Knitted Fabric)

A reaction solution was prepared by mixing, stirring and dissolving 46 wt % of nitrobenzene, 46 wt % of sulfuric acid, 1 wt % of paraformaldehyde, and 7 wt % of N-methylol-α-chloroacetamide (hereinafter, NMCA) at 10° C. or less (hereinafter, reaction solution for NMCA-ation). The reaction solution for NMCA-ation was cooled to 5° C., and 40 mL of the cooled reaction solution for NMCA-ation was added to 1 g of the knitted fabric, followed by reaction for two hours in a water bath while maintaining the reaction solution at 5° C. The knitted fabric was then taken out of the reaction solution, and submerged into and washed with the same amount of nitrobenzene as that of the NMCA reaction solution. The knitted fabric was then taken out, and submerged into and washed with methanol to obtain a chloroacetamidemethylated knitted fabric for Example 1. For a chloroacetamidemethylated knitted fabric for Example 4, a chloroacetamidemethylated knitted fabric for Example 5, a chloroacetamidemethylated knitted fabric for Example 6, and a chloroacetamidemethylated knitted fabric for Example 7, those knitted fabrics were obtained by each performing the same operations as the chloroacetamidemethylated knitted fabric for Example 1, except that the concentration of paraformaldehyde was changed to 0.85 wt %, 0.9 wt %, 0.95 wt %, 0.60 wt %, respectively. Herein, the chloroacetamidemethyl group corresponds to the reactive functional group. For a chloroacetamidemethylated knitted fabric for Comparative Example 1, a chloroacetamidemethylated knitted fabric for Comparative Example 3, and a chloroacetamidemethylated knitted fabric for Comparative Example 4, those knitted fabrics were obtained by each performing the same operations as the chloroacetamidemethylated knitted fabric for Example 1, except that the concentration of paraformaldehyde was changed to 4 wt %, 0.5 wt %, 3 wt %, respectively.

(Producing of Tetraethylenepentamine-p-chlorophenylated Knitted Fabric)

To a 500 mL of dimethyl sulfoxide (hereinafter, DMSO), tetraethylenepentamine (hereinafter, TEPA) and triethylamine were each dissolved such that the concentration of TEPA was 20 mM and the concentration of triethylamine is 473 mM respectively, and to the dissolved solution, 10 g of the chloroacetamidemethylated knitted fabric for Example 1 above was submerged and the resultant was reacted at 40° C. for three hours. The knitted fabric was washed three times with DMSO, then submerged into a solution in which p-chlorophenyl isocyanate was dissolved to a 500 mL of DMSO, such that its concentration was 20 mM, and the resultant was reacted at 30° C. for an hour. The knitted fabric was then taken out of the reaction solution, and the fabric was submerged into and washed with the same amount of DMSO as that of the reaction solution, then submerged into and washed with methanol, and then submerged into and washed with water to obtain the tetraethylenepentamine-p-chlorophenylated knitted fabric for Example 1.

A tetraethylenepentamine-p-chlorophenylated knitted fabric for Example 2 was obtained by carrying out the same operation as that of the tetraethylenepentamine-p-chlorophenylated knitted fabric for Example 1, except that the concentration of TEPA was changed from 20 mM to 40 mM. A tetraethylenepentamine-p-chlorophenylated knitted fabric for Example 3 was obtained by carrying out the same operation as that of the tetraethylenepentamine-p-chlorophenylated knitted fabric for Example 1, except that the concentration of TEPA was changed from 20 mM to 10 mM. Each of tetraethylenepentamine-p-chlorophenylated knitted fabrics for Examples 4 to 6 was obtained by using chloroacetamidemethylated knitted fabrics for Examples 4 to 6, respectively, instead of the chloroacetamidemethylated knitted fabric for Example 1, and by carrying out the same operation as that of the tetraethylenepentamine-p-chlorophenylated knitted fabric for Example 1, except that the concentration of TEPA was changed from 20 mM to 10 mM. A tetraethylenepentamine-p-chlorophenylated knitted fabric for Example 7 was obtained by using a chloroacetamidemethylated knitted fabric for Example 7, instead of the chloroacetamidemethylated knitted fabric for Example 1, and by carrying out the same operation as that of the tetraethylenepentamine-p-chlorophenylated knitted fabric for Example 1, except that the concentration of TEPA was changed from 20 mM to 40 mM.

A tetraethylenepentamine-p-chlorophenylated knitted fabric for Comparative Example 1 was also obtained by using a chloroacetamidemethylated knitted fabric for Comparative Example 1, and by carrying out the same operation as that of the tetraethylenepentamine-p-chlorophenylated knitted fabric for Example 1, except that the concentration of TEPA was changed from 20 mM to 40 mM. A tetraethylenepentamine-p-chlorophenylated knitted fabric for Comparative Example 2 was obtained by using a chloroacetamidemethylated knitted fabric for Comparative Example 1, and by carrying out the same operation as that of the tetraethylenepentamine-p-chlorophenylated knitted fabric for Example 1, except that the concentration of TEPA was changed from 20 mM to 10 mM. A tetraethylenepentamine-p-chlorophenylated knitted fabric for Comparative Example 3 was obtained by using a chloroacetamidemethylated knitted fabric for Comparative Example 3, and by carrying out the same operation as that of the tetraethylenepentamine-p-chlorophenylated knitted fabric for Example 1, except that the concentration of TEPA was changed from 20 mM to 5 mM. A tetraethylenepentamine-p-chlorophenylated control knitted fabric for Comparative Example 4 was obtained by using a chloroacetamidemethylated knitted fabric for Comparative Example 4 and carrying out the same operation as that of the tetraethylenepentamine-p-chlorophenylated knitted fabric for Example 1, except that the concentration of TEPA was changed from 20 mM to 0 mM.

(1) Measurement of Extending Length Ratio (Rlr)

Examples 1 to 7

For the tetraethylenepentamine-p-chlorophenylated knitted fabric for Example 1 produced above, images were captured by using the laser microscope (Ultra-Depth Color 3D Dimensional Measurement Microscope VK-9710, manufactured by KEYENCE Corp.), a profile in the obtained image is extracted by the sampling length of 50 μm (corresponding to l) in its mean line direction, and the extracted profile was analyzed using an analysis software loaded with the VK-9710 in a line roughness mode to calculate the extending length ratio (Rlr). As the condition for capturing the images for the laser microscope, the objective lens was set to 20 times. The foregoing knitted fabric was put on a slide glass with the fabric being wet with distilled water, the fabric was covered with a cover glass (thickness: 0.12 to 0.17 mm) from above, excess distilled water was removed, and then images were captured from above the cover glass. Table 2 shows the average value of the results in nine fields of view. For the tetraethylenepentamine-p-chlorophenylated knitted fabrics for Examples 2 to 7, the same operations were carried out. The results are shown in Table 2.

Comparative Examples 1 to 4

For the tetraethylenepentamine-p-chlorophenylated knitted fabric for Comparative Example 1 produced above, images were captured by using the laser microscope (Ultra-Depth Color 3D Dimensional Measurement Microscope VK-9710, manufactured by KEYENCE Corp.), a profile in the obtained image was extracted by the sampling length of 50 μm (corresponding to l) in its mean line direction to calculate the extending length ratio (Rlr) in the same manner as Example 1. Table 2 shows the average value of the results in nine fields of view. For the tetraethylenepentamine-p-chlorophenylated knitted fabrics for Comparative Examples 2 and 3, and the tetraethylenepentamine-p-chlorophenyl control knitted fabric for Comparative Example 4, the same operations were carried out. The results are shown in Table 2.

Comparative Example 5

For sepXiris® (Baxter Limited, Medical Equipment Approval No. 22500BZX00401000) approved as a slow continuous hemofilter with a hollow-fiber membrane, inner surface of a hollow fiber (hereinafter, hollow fiber of Comparative Example 5) was exposed by tearing the hollow fiber in the longitudinal direction of the fiber, images for the inner surface were captured by using the laser microscope (Ultra-Depth Color 3D Dimensional Measurement Microscope VK-9710, manufactured by KEYENCE Corp.), a profile in the obtained image was extracted by the sampling length of 50 μm (corresponding to l) in its mean line direction to calculate the extending length ratio (Rlr) in the same manner as Example 1. Table 2 shows the average value of the results in nine fields of view.

Comparative Example 6

For CytoSorb® (CytoSorbents Corporation) commercially available overseas as a hemoperfusion adsorption column comprising polystyrene beads coated with biocompatible polymer, the bead (hereinafter, beads of Comparative Example 6) was split, and images for the surface of the bead were captured by using the laser microscope (Ultra-Depth Color 3D Dimensional Measurement Microscope VK-9710, manufactured by KEYENCE Corp.), and a profile in the obtained image was extracted by the sampling length of 50 μm (corresponding to l) in its mean line direction to calculate the extending length ratio (Rlr) in the same manner as Example 1. Table 2 shows the average value of the results in nine fields of view.

Comparative Example 7

For Adacolumn® (JIMRO Co., Ltd., Medical Equipment Approval No. 21100BZZ00687000) commercially available as a hemoperfusion adsorption column comprising cellulose acetate beads, the bead (hereinafter, beads of Comparative Example 7) was split, and images for the surface of the bead were captured by using the laser microscope (Ultra-Depth Color 3D Dimensional Measurement Microscope VK-9710, manufactured by KEYENCE Corp.), and a profile in the obtained image was extracted by the sampling length of 50 μm (corresponding to l) in its mean line direction to calculate the extending length ratio (Rlr) in the same manner as Example 1. Table 2 shows the average value of the results in nine fields of view.

(2) Measurement of Center Line Mean Roughness (Ra) (μm)

Examples 1 to 7

For the tetraethylenepentamine-p-chlorophenylated knitted fabric for Example 1 produced above, images were captured by using the laser microscope (Ultra-Depth Color 3D Dimensional Measurement Microscope VK-9710, manufactured by KEYENCE Corp.), a profile in the obtained image was extracted by the sampling length of 50 μm (corresponding to l) in its mean line direction, the extracted profile was analyzed using an analysis software loaded with the VK-9710 in a line roughness mode to calculate the center line mean roughness (Ra). As the condition for capturing images of the laser microscope, the objective lens was set to 20 times. The foregoing knitted fabric was put on a slide glass with the fabric being wet with distilled water, the fabric was covered with a cover glass (thickness: 0.12 to 0.17 mm) from above, excess distilled water was removed, and then images was captured from above the cover glass. Table 2 shows the average value of the results in nine fields of view. For the tetraethylenepentamine-p-chlorophenylated knitted fabrics for Examples 2 to 7, the same operations were carried out. The results are shown in Table 2.

Comparative Examples 1 to 4

For the tetraethylenepentamine-p-chlorophenylated knitted fabric for Comparative Example 1 produced above, images were captured by using the laser microscope (Ultra-Depth Color 3D Dimensional Measurement Microscope VK-9710, manufactured by KEYENCE Corp.), a profile in the obtained image was extracted by the sampling length of 50 μm (corresponding to l) in its mean line direction to calculate the center line mean roughness (Ra) in the same manner as Example 1. Table 2 shows the average value of the results in nine fields of view. For the tetraethylenepentamine-p-chlorophenylated knitted fabrics for Comparative Examples 2 and 3, and the tetraethylenepentamine-p-chlorophenyl control knitted fabric for Comparative Example 4, the same operations were carried out. The results are shown in Table 2.

Comparative Example 5

For the hollow fiber of Comparative Example 5, after exposing its inner surface by tearing the hollow fiber in the longitudinal direction of the fiber, images of the inner surface were captured by using the laser microscope (Ultra-Depth Color 3D Dimensional Measurement Microscope VK-9710, manufactured by KEYENCE Corp.), a profile in the obtained image was extracted by the sampling length of 50 μm (corresponding to l) in its mean line direction to calculate the center line mean roughness (Ra) in the same manner as Example 1. Table 2 shows the average value of the results in nine fields of view.

Comparative Example 6

For the beads of Comparative Example 6, after a bead was split, images of the surface of the bead were captured by using the laser microscope (Ultra-Depth Color 3D Dimensional Measurement Microscope VK-9710, manufactured by KEYENCE Corp.), a profile in the obtained image was extracted by the sampling length of 50 μm (corresponding to l) in its mean line direction to calculate the center line mean roughness (Ra) in the same manner as Example 1. Table 2 shows the average value of the results in nine fields of view.

Comparative Example 7

For the beads of Comparative Example 7, after a bead was split, images of the surface of the bead were captured by using the laser microscope (Ultra-Depth Color 3D Dimensional Measurement Microscope VK-9710, manufactured by KEYENCE Corp.), and a profile in the obtained image was extracted by the sampling length of 50 μm (corresponding to l) in its mean line direction to calculate the center line mean roughness (Ra) in the same manner as Example 1. Table 2 shows the average value of the results in nine fields of view.

(3) Measurement of Root Mean Square Slope Angle (°)

Examples 1 to 7

For the tetraethylenepentamine-p-chlorophenylated knitted fabric for Example 1 produced above, images were captured by using the laser microscope (Ultra-Depth Color 3D Dimensional Measurement Microscope VK-9710, manufactured by KEYENCE Corp.), a profile in the obtained image was extracted by the sampling length of 50 μm (corresponding to l) in its mean line direction, and the extracted profile was analyzed using an analysis software loaded with the VK-9710 in a line roughness mode to calculate the root mean square slope angle. As the condition for capturing the images for the laser microscope, the objective lens was set to 20 times. The foregoing knitted fabric was put on a slide glass with the fabric being wet with distilled water, the fabric was covered with a cover glass (thickness: 0.12 to 0.17 mm) from above, excess distilled water was removed, and then images were captured from above the cover glass. Table 2 shows the average value of the results in nine fields of view. For the tetraethylenepentamine-p-chlorophenylated knitted fabrics for Examples 2 to 7, the same operations were carried out. The results are shown in Table 2.

Comparative Examples 1 to 4

For the tetraethylenepentamine-p-chlorophenylated knitted fabric for Comparative Example 1 produced above, images were captured by using the laser microscope (Ultra-Depth Color 3D Dimensional Measurement Microscope VK-9710, manufactured by KEYENCE Corp.), and a profile in the obtained image was extracted by the sampling length of 50 μm (corresponding to l) in its mean line direction to calculate the root mean square slope angle in the same manner as Example 1. Table 2 shows the average value of the results in nine fields of view. For the tetraethylenepentamine-p-chlorophenylated knitted fabrics for Comparative Examples 2 and 3, and the tetraethylenepentamine-p-chlorophenyl control knitted fabric for Comparative Example 4, the same operations were carried out. The results are shown in Table 2.

Comparative Example 5

For the hollow fiber of Comparative Example 5, after exposing its inner surface by tearing the hollow fiber in the longitudinal direction of the fiber, images of the inner surface were captured by using the laser microscope (Ultra-Depth Color 3D Dimensional Measurement Microscope VK-9710, manufactured by KEYENCE Corp.), and a profile in the obtained image was extracted by the sampling length of 50 μm (corresponding to l) in its mean line direction to calculate the root mean square slope angle in the same manner as Example 1. Table 2 shows the average value of the results in nine fields of view.

Comparative Example 6

For the beads of Comparative Example 6, after a bead was split, images of the surface of the bead were captured by using the laser microscope (Ultra-Depth Color 3D Dimensional Measurement Microscope VK-9710, manufactured by KEYENCE Corp.), and a profile in the obtained image was extracted by the sampling length of 50 μm (corresponding to l) in its mean line direction to calculate the root mean square slope angle in the same manner as Example 1. Table 2 shows the average value of the results in nine fields of view.

Comparative Example 7

For the beads of Comparative Example 7, after a bead was split, images of the surface of the bead were captured by using the laser microscope (Ultra-Depth Color 3D Dimensional Measurement Microscope VK-9710, manufactured by KEYENCE Corp.), and a profile in the obtained image was extracted by the sampling length of 50 μm (corresponding to l) in its mean line direction to calculate the center root mean square slope angle in the same manner as Example 1. Table 2 shows the average value of the results in nine fields of view.

(4) Measurement of Positive Charge Amount

Examples 1 to 7, Comparative Examples 1 to 7

A positive charge amount included in the tetraethylenepentamine-p-chlorophenylated knitted fabric for Example 1 was determined by acid-base back titration. To a 200-mL recovery flask, the tetraethylenepentamine-p-chlorophenylated knitted fabric for Example 1 was added with 50 mL of 6M aqueous sodium hydroxide, and the resulting solution was stirred for 30 minutes. The knitted fabric was filtrated through a filter paper. Then, the filtrated knitted fabric was added to 50 mL of ion-exchanged water, and the resultant was stirred for 30 minutes and the filtrated through a filter paper. The addition of the knitted fabric to ion-exchanged water and filtration of the knitted fabric were repeated until the pH of the ion-exchanged water reaches to 7.0 to obtain the desalted knitted fabric. After the desalted knitted fabric was left to stand at 80° C. under normal pressure conditions for 48 hours, 1.0 g of the dried knitted fabric and 30 mL of 0.1 M hydrochloric acid were added to a polypropylene container and the resultant solution was stirred for 10 minutes. After the stirring, 5 mL of the solution alone was pulled out and transferred into a polypropylene container. Then, to the obtained solution, 0.1 mL of a 0.1 M sodium hydroxide aqueous solution was added dropwise. After dropwise addition, the resulting solution was stirred for 10 minutes, and the pH of the solution was measured. The operation of dropwise addition of 0.1 mL of the 0.1 M sodium hydroxide aqueous solution followed by the 10-minute stirring and pH measurement, was repeated 100 times in the same manner. The amount of the 0.1 M sodium hydroxide aqueous solution added dropwise when the pH of the solution exceeded 8.5 was regarded as a titer per 1.0 g. Using the titer per 1.0 g and the following Equation 4, the positive charge amount of the tetraethylenepentamine-p-chlorophenylated knitted fabric for Example 1 was calculated. The results are shown in Table 2.

Positive Charge Amount per 1 g Dry Weight (mmol/g)={Added 0.1 M Hydrochloric Acid Liquid Amount (30 mL)/Pulled-out Hydrochloric Acid Liquid Amount (5 mL)}×Titer per 1.0 g (mL/g)×Sodium Hydroxide Aqueous Solution Concentration (0.1 M)    Equation 4

For the tetraethylenepentamine-p-chlorophenylated knitted fabrics for Examples 2 to 7, the tetraethylenepentamine-p-chlorophenylated knitted fabrics for Comparative Examples 1 to 3, the tetraethylenepentamine-p-chlorophenyl control knitted fabric for Comparative Example 4, the hollow fiber of Comparative Example 5, the beads of Comparative Example 6 and the beads of Comparative Example 7, the same operations were carried out. The results are shown in Table 2.

(5) Measurement of Removal Rate of Activated Granulocyte-Activated Platelet Complex, Activated Monocyte-Activated Platelet Complex, Activated Granulocyte, and Activated Monocyte Examples 1 to 7

Disks, 1 cm in diameter, cut out of the tetraethylenepentamine-p-chlorophenylated knitted fabrics for Example 1 were packed by stacking them in a cylindrical column having a solution inlet and a solution outlet at the top and bottom (1 cm in internal diameter×1.2 cm in height, 0.94 cm³ in internal volume, 2 cm in external diameter, made of polycarbonate), to thereby produce the column including the tetraethylenepentamine-p-chlorophenylated knitted fabrics for Example 1. LPS was added to blood of a healthy human volunteer to become 70 EU/mL, the resulting blood was shaken and activated under the conditions of at 65 rpm, at 37° C., for 30 minutes in a water bath, the activated blood was passed through the column at a flow rate of 0.63 mL/min using a pump, and blood samples were taken at the inlet and outlet of the column. The sample from the column inlet was taken from the blood that was immersed in the water bath. Assuming that the time when the blood flowed into the column was at a time point of 0 minute, the blood sample from the column outlet was taken from the blood that had passed through the column for 3.5 to 6.5 minutes. The cell surface antigens of the samples obtained after the blood was passed through the column were stained with a fluorescently-labeled antibody shown in Table 1, and then the samples were subjected to hemolysis using VersaLyse, left to stand, then cooled on ice, and stored in a dark place, followed by promptly measuring the number of cells contained in each sample. In this regard, 7-AAD Viability Staining Solution (Biolegend) was used to discriminate living cells, and Flow Count (BECKMAN COULTER) was used to count the number of cells. For measurement, flow cytometry (BD Cytometer Setup and Tracking Beads (Becton, Dickinson and Company)) was used. For analysis, BD FACS Diva software Version 6.1.3 (Becton, Dickinson and Company) or FLOWJO (Tomy Digital Biology Co., Ltd.) was used. The concentrations of an activated granulocyte-activated platelet complex, an activated monocyte-activated platelet complex, an activated granulocyte, and an activated monocyte were calculated, followed by calculating the respective removal rates before entry into and after exiting out of the column, using the following Equation 5 to Equation 8. The column created without the knitted fabric was used as an empty column, and the same blood-passed-through test as one described above was performed to obtain each removal rate, which was used as the removal rate for each component in the empty column, and a ratio of removal ability relative to the empty column was calculated according to the following Equation 9 to Equation 12. The results are shown in Table 3.

Activated Granulocyte-Activated Platelet Complex Removal Rate (%)={(Activated Granulocyte-Activated Platelet Complex Concentration at Column Inlet Side)−(Activated Granulocyte-Activated Platelet Complex Concentration at Column Outlet Side)}/(Activated Granulocyte-Activated Platelet Complex Concentration at Column Inlet Side)×100    Equation 5

Activated Monocyte-Activated Platelet Complex Removal Rate (%)={(Activated Monocyte-Activated Platelet Complex Concentration at Column Inlet Side)−(Activated Monocyte-Activated Platelet Complex Concentration at Column Outlet Side)}/(Activated Monocyte-Activated Platelet Complex Concentration at Column Inlet Side)×100    Equation 6

Activated Granulocyte Removal Rate (%)={(Activated Granulocyte Concentration at Column Inlet Side)−(Activated Granulocyte Concentration at Column Outlet Side)}/(Activated Granulocyte Concentration at Column Inlet Side)×100    Equation 7

Interstitial

Activated Monocyte Removal Rate (%)={(Activated Monocyte Concentration at Column Inlet Side)−(Activated Monocyte Concentration at Column Outlet Side)}/(Activated Monocyte Concentration at Column Inlet Side)×100    Equation 8

Activated Granulocyte-Activated Platelet Complex Removal Ability (Ratio to Empty Column)=Activated Granulocyte-Activated Platelet Complex Removal Rate in Each Example (%)/Activated Granulocyte-Activated Platelet Complex Removal Rate in Empty Column (%)    Equation 9

Activated Monocyte-Activated Platelet Complex Removal Ability (Ratio to Empty Column)=Activated Monocyte-Activated Platelet Complex Removal Rate in Each Example (%)/Activated Monocyte-Activated Platelet Complex Removal Rate in Empty Column (%)    Equation 10

Activated Granulocyte Removal Ability (Ratio to Empty Column)=Activated Granulocyte Removal Rate in Each Example (%)/Activated Granulocyte Removal Rate in Empty Column (%)    Equation 11

Activated Monocyte Removal Ability (Ratio to Empty Column)=Activated Monocyte Removal Rate in Each Example (%)/Activated Monocyte Removal Rate in Empty Column (%)    Equation 12

TABLE 1

| Antibody Name | Manufacturer | Catalog No. |
|---|---|---|
| APC Mouse Anti-Human CD11b (activated) | BioLegend | 301410 |
| PE/Cy7 Mouse Anti-Human CD14 | BioLegend | 556619 |
| BV510 Mouse Anti-Human CD45 | BioLegend | 304036 |
| BV421 Mouse Anti-Human CD62P | BioLegend | 304926 |
| FITC Mouse Anti-Human CD66b | BioLegend | 557749 |
| APC Mouse IgG1 Isotype Control | BD Biosciences | 340442 |
| PE/Cy7 Mouse IgG2a Isotype Control | BioLegend | 400232 |
| BV510 Mouse IgG1 Isotype Control | BioLegend | 400172 |
| BV421 Mouse IgG1κ, Isotype Control | BioLegend | 400158 |
| FITC Mouse IgM Isotyne Control | BD Biosciences | 349041 |

For the tetraethylenepentamine-p-chlorophenylated knitted fabrics for Examples 2 to 7, the same operations were carried out. The results are shown in Table 3.

Comparative Examples 1 to 4

Disks, 1 cm in diameter, cut out of the tetraethylenepentamine-p-chlorophenylated knitted fabrics for Comparative Example 1 were packed by stacking them in a cylindrical column having a solution inlet and a solution outlet at the top and bottom (1 cm in internal diameter×1.2 cm in height, 0.94 cm$^3$ in internal volume, 2 cm in external diameter, made of polycarbonate), to thereby produce the column including the tetraethylenepentamine-p-chlorophenylated knitted fabrics for Comparative Example 1. The concentrations of activated granulocyte-activated platelet complex, an activated monocyte-activated platelet complex, an activated granulocyte, and an activated monocyte were calculated in the same manner as Example 1, followed by calculating a ratio of each removal ability relative to the empty column, using the Equation 5 to Equation 12 above. For the tetraethylenepentamine-p-chlorophenylated knitted fabrics for Comparative Examples 2 and 3, and the tetraethylenepentamine-p-chlorophenyl control knitted fabric for Comparative Example 4, the same operations were carried out. The results are shown in Table 3.

Comparative Example 5

For sepXiris®, the hollow fiber of Comparative Example 5 was cut to 10 cm×157 fibers to produce a mini module. The concentrations of an activated granulocyte-activated platelet complex, an activated monocyte-activated platelet complex, an activated granulocyte, and an activated monocyte were calculated in the same manner as Example 1, followed by calculating a ratio of each removal ability relative to the empty column, using the Equation 5 to Equation 12 above. The results are shown in Table 3.

Comparative Example 6

For CytoSorb®, 1.13 mL of the beads of Comparative Example 6 was taken out to produce a mini module. The concentrations of an activated granulocyte-activated platelet complex, an activated monocyte-activated platelet complex, an activated granulocyte, and an activated monocyte were calculated in the same manner as Example 1, followed by calculating a ratio of each removal ability relative to the empty column, using the Equation 5 to Equation 12 above. The results are shown in Table 3.

Comparative Example 7

For Adacolumn®, 1.63 g of the beads of Comparative Example 7 was taken out to produce a mini module. The concentrations of an activated granulocyte-activated platelet complex, an activated monocyte-activated platelet complex, an activated granulocyte, and an activated monocyte were calculated in the same manner as Example 1, followed by calculating a ratio of each removal ability relative to the empty column, using the Equation 5 to Equation 12 above. The results are shown in Table 3.

(6) Measurement of Removal Rate of IL-6

Examples 1 to 7

The tetraethylenepentamine-p-chlorophenylated knitted fabric for Example 1 was cut into disks having a diameter of 6 mm, four of which were put into a polypropylene container. To the container, 1 ml of fetal bovine serum (hereinafter, FBS) that was prepared such that the concentration of IL-6 is 2000 pg/mL was added, the resulting mixture was mixed by inversion for two hours in an incubator at 37° C., and then the remaining concentration of IL-6 was measured by ELISA, thus calculating the removal rate of IL-6 using the following Equation 13. The results are shown in Table 4.

Removal Rate of IL-6 (%)={(concentration of IL-6 before mixed by inversion)−(concentration of IL-6 after mixed by inversion)}/(concentration of IL-6 before mixed by inversion)×100    Equation 13

For the tetraethylenepentamine-p-chlorophenylated knitted fabrics for Examples 2 to 7, the same operations were carried out. The results are shown in Table 4.

Comparative Examples 1 to 4

The tetraethylenepentamine-p-chlorophenylated knitted fabric for Comparative Example 1 was cut into disks having a diameter of 6 mm, four of which were put into a polypropylene container. To the container, 1 ml of FBS that was prepared such that the concentration of IL-6 is 2000 pg/mL similarly was added, the resultant mixture was mixed by inversion for two hours in an incubator at 37° C., and then a remaining concentration of IL-6 was measured by ELISA, thus calculating the removal rate of IL-6 using the forgoing Equation 13. The results are shown in Table 4. For the tetraethylenepentamine-p-chlorophenylated knitted fabrics for Comparative Examples 2 and 3, and the tetraethylenepentamine-p-chlorophenyl control knitted fabric for Comparative Example 4, the same operations were carried out. The results are shown in Table 4.

Comparative Example 5

For sepXiris®, the hollow fiber of Comparative Example 5 was cut to 50 cm length, and the cut fiber was put into a polypropylene container. To the container, 1 ml of FBS that was prepared such that the concentration of IL-6 is 2000 pg/mL similarly was added, the resultant was mixed by inversion for two hours in an incubator at 37° C., and then a remaining concentration of IL-6 thereinside was measured by ELISA, thus calculating the removal rate of IL-6 using the forgoing Equation 13. The results are shown in Table 4.

Comparative Example 6

For CytoSorb®, 50 μL of the beads of Comparative Example 6 was taken out into a polypropylene container. To the container, 1 ml of FBS that was prepared such that the concentration of IL-6 is 2000 pg/mL similarly was added, the resultant was mixed by inversion for two hours in an incubator at 37° C., and then a remaining concentration of IL-6 thereinside was measured by ELISA, thus calculating the removal rate of IL-6 using the forgoing Equation 13. The results are shown in Table 4.

Comparative Example 7

For Adacolumn®, 75 mg of the beads of Comparative Example 7 was taken out into a polypropylene container. To the container, 1 ml of FBS that was prepared such that the concentration of IL-6 is 2000 pg/mL similarly was added, the resultant was mixed by inversion for two hours in an incubator at 37° C., and then a remaining concentration of IL-6 thereinside was measured by ELISA, thus calculating the removal rate of IL-6 using the forgoing Equation 13. The results are shown in Table 4.

(7) Measurement of Removal Rate of IL-8

Examples 1 to 7

The tetraethylenepentamine-p-chlorophenylated knitted fabric for Example 1 was cut into disks having a diameter of 6 mm, four of which were put into a polypropylene container. To the container, 1 ml of fetal bovine serum (hereinafter, FBS) that was prepared such that the concentration of IL-8 is 2000 pg/mL was added, the resultant was mixed by inversion for one hour in an incubator at 37° C., and then a remaining concentration of IL-6 was measured by ELISA, thus calculating the removal rate of IL-8 using the following Equation 14. The results are shown in Table 4.

Removal Rate of IL-8 (%)={(concentration of IL-8 before mixed by inversion)−(concentration of IL-8 after mixed by inversion)}/(concentration of IL-8 before mixed by inversion)×100    Equation 14

For the tetraethylenepentamine-p-chlorophenylated knitted fabrics for Examples 2 to 6, the same operations were carried out. The results are shown in Table 4.

Comparative Examples 1 to 4

The tetraethylenepentamine-p-chlorophenylated knitted fabric for Comparative Example 1 was cut into disks having a diameter of 6 mm, four of which were put into a polypropylene container. To the container, 1 ml of FBS that was prepared such that the concentration of IL-8 is 2000 pg/mL similarly was added, the resultant was mixed by inversion for one hour in an incubator at 37° C., and then a remaining concentration of IL-8 was measured by ELISA, thus calculating the removal rate of IL-8 using the forgoing Equation 14. The results are shown in Table 4. For the tetraethylenepentamine-p-chlorophenylated knitted fabrics for Comparative Examples 2 and 3, and the tetraethylenepentamine-p-chlorophenyl control knitted fabric for Comparative Example 4, the same operations were carried out. The results are shown in Table 4.

Comparative Example 5

For sepXiris®, the hollow fiber of Comparative Example 5 was cut to 50 cm length, the cut fiber was put into a polypropylene container. To the container, 1 ml of FBS that was prepared such that the concentration of IL-8 is 2000 pg/mL similarly was added, the resultant was mixed by inversion for one hour in an incubator at 37° C., and then a remaining concentration of IL-8 was measured by ELISA, thus calculating the removal rate of IL-8 using the forgoing Equation 14. The results are shown in Table 4.

Comparative Example 6

For CytoSorb®, 50 μL of the beads of Comparative Example 6 was taken out into a polypropylene container. To the container, 1 ml of FBS that was prepared such that the concentration of IL-8 is 2000 pg/mL similarly was added, the resultant was mixed by inversion for one hour in an incubator at 37° C., and then a remaining concentration of IL-8 was measured by ELISA, thus calculating the removal rate of IL-8 using the forgoing Equation 14. The results are shown in Table 4.

Comparative Example 7

For Adacolumn®, 75 mg of the beads of Comparative Example 7 was taken out into a polypropylene container. To the container, 1 ml of FBS that was prepared such that the concentration of IL-8 is 2000 pg/mL similarly was added, the resultant was mixed by inversion for two hours in an incubator at 37° C., and then a remaining concentration of IL-8 was measured by ELISA, thus calculating the removal rate of IL-8 using the forgoing Equation 14. The results are shown in Table 4.

(8) Measurement of Removal Rate of HMGB-1

Examples 1 to 7

The tetraethylenepentamine-p-chlorophenylated knitted fabric for Example 1 was cut into disks having a diameter of 6 mm, four of which were put into a polypropylene container. To the container, 1 ml of fetal bovine serum (hereinafter, FBS) that was prepared such that the concentration of HMGB-1 is 100 ng/mL was added, the resultant was mixed by inversion for one hour in an incubator at 37° C., and then a remaining concentration of IL-6 was measured by ELISA, thus calculating the removal rate of HMGB-1 using the following Equation 15. The results are shown in Table 4.

Removal Rate of HMGB-1 (%)={(concentration of HMGB-1 before mixed by inversion)−(concentration of HMGB-1 after mixed by inversion)}/(concentration of HMGB-1 before mixed by inversion)×100     Equation 15

For the tetraethylenepentamine-p-chlorophenylated knitted fabrics for Examples 2 to 6, the same operations were carried out. The results are shown in Table 4.

Comparative Examples 1 to 4

The tetraethylenepentamine-p-chlorophenylated knitted fabric for Comparative Example 1 was cut into disks having a diameter of 6 mm, four of which were put into a polypropylene container. To the container, 1 ml of FBS that was prepared such that the concentration of HMGB-1 is 100 ng/mL similarly was added, the resultant was mixed by inversion for one hour in an incubator at 37° C., and then a remaining concentration of HMGB-1 was measured by ELISA, thus calculating the removal rate of HMGB-1 using the forgoing Equation 15. The results are shown in Table 4. For the tetraethylenepentamine-p-chlorophenylated knitted fabrics for Comparative Examples 2 and 3, and the tetraethylenepentamine-p-chlorophenyl control knitted fabric for Comparative Example 4, the same operations were carried out. The results are shown in Table 4.

Comparative Example 5

For sepXiris®, the hollow fiber of Comparative Example 5 was cut to 50 cm length, the cut fiber was put into a polypropylene container. To the container, 1 ml of FBS that was prepared such that the concentration of HMGB-1 is 100 ng/mL similarly was added, the resultant was mixed by inversion for one hour in an incubator at 37° C., and then a remaining concentration of HMGB-1 was measured by ELISA, thus calculating the removal rate of HMGB-1 using the forgoing Equation 15. The results are shown in Table 4.

Comparative Example 6

For CytoSorb®, 50 μL of the beads of Comparative Example 6 was taken out into a polypropylene container. To the container, 1 ml of FBS that was prepared such that the concentration of HMGB-1 is 100 ng/mL similarly was added, the resultant was mixed by inversion for one hour in an incubator at 37° C., and then a remaining concentration of HMGB-1 was measured by ELISA, thus calculating the removal rate of HMGB-1 using the forgoing Equation 15. The results are shown in Table 4.

Comparative Example 7

For Adacolumn®, 75 mg of the beads of Comparative Example 7 was taken out into a polypropylene container. To the container, 1 ml of FBS that was prepared such that the concentration of HMGB-1 is 100 ng/mL similarly was added, the resultant was mixed by inversion for two hours in an incubator at 37° C., and then a remaining concentration of HMGB-1 was measured by ELISA, thus calculating the removal rate of HMGB-1 using the forgoing Equation 15. The results are shown in Table 4.

(9) Evaluation for Inhibition of Pulmonary Function (P/F) Decline

Examples 1 to 6, Comparative Examples 1 to 7

Inhibitory effect of pulmonary function (P/F) decline was evaluated, using a rabbit, through ARDS model produced by intratracheal administration of HCl and LPS (Reference: Japan Geriatrics Society Journal, Vol. 30, 1032-1038 (1993)). First, after anesthesia induction through intravenous administration of 30 mg/kg of pentobarbital sodium (25 mg/mL, NACALAI TESQUE, INC.), a NZW male rabbit (body weight: 3 to 3.5 kg) was shaved at the neck and abdomen. After subcutaneous injection of lidocaine (Xylocaine Injection 0.5%, AstraZeneca K.K.), the trachea was exposed from the neck. A tracheal cannula (16 Fr, Terumo Corporation) was intubated and immobilized to the trachea. A respirator (EVITA 300, Draeger Medical Japan LTD.) was used to perform ventilation. Conditions of the ventilation were regulated by measuring parameters of blood gas of blood collected from a carotid artery with PEEP applied through i-STAT (cartridge CG4+, ABBOTT JAPAN CO., LTD.) and changing the number of ventilation such that the measurements (values corrected to a body temperature) before administration of HCl and LPS were within the $pCO_2$ range of 35 to 45 mmHg. An inspired oxygen concentration was set to 100%, and after the conditions of the ventilation is set, evaluation of the equipment to be tested was started. During the evaluation, the conditions of the ventilation were not changed. An infusion of 0.06 mg/kg/hr of vecuronium dissolved in normal saline (VECURONIUM 4 mg for intravenous injection: Fuji Pharma, Co., Ltd., normal saline: Otsuka Pharmaceutical Factory, Inc.) was given by continuous infusion of 2 mL/kg/hr. The infusion was further connected to an infusion pump (55-1111, HARVARD APPARATUS, INC.) via a three way stopcock to achieve a route of maintenance anesthesia. As maintenance anesthesia, pentobarbital (12.5 mg/mL, NACALAI TESQUE, INC.) was given by continuous infusion of 2 to 8 mg/kg/hr (decreased or increased in accordance with state of the animal). ARDS was induced by intratracheal administration of 2 mL/kg of 0.04 N HCl, and by intratracheal administration of 3 mL/kg of 0.05 mg/kg LPS at 30 minutes after the administration of HCl. Assuming that the time point at which LPS was administrated was regarded as the time 0 hour, the inhibitory effect of pulmonary function (P/F) decline was evaluated from P/F at 6 hours after the administration. For Examples 1 to 6 and Comparative Examples 1 to 4, the tetraethylenepentamine-p-chlorophenylated knitted fabrics for Examples 1 to 6 and Comparative Examples 1 to 3 and the tetraethylenepentamine-p-chlorophenylated control knitted fabric for Comparative Example 4 produced by the foregoing procedures were each packed in each cylindrical mini column having a packing volume of 11 cm³ (packing height: 4.7 cm, packing diameter: 1.9 cm) to produce columns for treatment of ARDS for model animals. For Comparative Example 5, sepXiris® was used to produce a mini column having a membrane area of 750 cm² (effective length: 10 cm). For Comparative Example 6, CytoSorb® was used to produce a mini column having a packing amount of the beads of 13.5 mL (packing height: 4.7 cm, packing diameter: 1.9 cm). For Comparative Example 7, Adacolumn® was used to produce a mini column having a packing amount of the beads of 19.6 g (packing height: 4.7 cm, packing diameter: 1.9 cm). Each column was washed with normal saline, and after priming a heparin, each column was executed at a flow rate of 5 mL/min to the ARDS-induced rabbit immediately after intratracheal administration of LPS, and the pulmonary function (P/F) was evaluated at 6 hours after the administration. The results of the evaluation are shown in Table 4. As the evaluation of effectiveness, when the P/F value is greater than 300, the column was defined as being effective, and when the P/F value is 300 or less, the column was defined as no effect because the value was fell within the ARDS criteria (ARDS standard value by Berlin definition, Reference: JAMA. 2012; 307 (23): 2526-2533).

TABLE 2

| | Center Line Average Roughness Ra [μm] | Extending Length Ratio Rlr [—] | Root Mean Square Slope Angle [°] | Positive Charge Amount [mmol/g] |
|---|---|---|---|---|
| Example 1 | 2.33 | 5.88 | 73.6 | 1.05 |
| Example 2 | 2.93 | 4.30 | 80.2 | 2.61 |
| Example 3 | 2.11 | 6.06 | 55.2 | 0.52 |
| Example 4 | 3.41 | 6.80 | 78.0 | 0.84 |
| Example 5 | 3.29 | 6.02 | 67.4 | 0.64 |
| Example 6 | 3.10 | 6.30 | 62.8 | 0.51 |
| Example 7 | 6.50 | 6.90 | 84.3 | 2.58 |
| Comparative Example 1 | 1.52 | 3.86 | 38.1 | 2.85 |
| Comparative Example 2 | 1.21 | 2.90 | 14.8 | 0.54 |
| Comparative Example 3 | 1.86 | 7.42 | 26.0 | 0.16 |
| Comparative Example 4 | 1.25 | 3.68 | 35.4 | 0.00 |
| Comparative Example 5 | 0.08 | 1.04 | 11.3 | 0.12 |
| Comparative Example 6 | 1.87 | 2.33 | 47.2 | 0.00 |
| Comparative Example 7 | 1.92 | 2.78 | 38.0 | 0.00 |

TABLE 3

Removal Ability of Blood Cells (Ratio to Empty Column)

| | Activated Granulocyte-Activated Platelet Complex | Activated Monocyte-Activated Platelet Complex | Activated Granulocyte | Activated Monocyte |
|---|---|---|---|---|
| Example 1 | 3.4 | 2.6 | 2.3 | 2.6 |
| Example 2 | 5.1 | 4.3 | 2.4 | 3.5 |
| Example 3 | 4.3 | 3.2 | 1.1 | 1.9 |
| Example 4 | 4.5 | 3.3 | 1.4 | 2.2 |
| Example 5 | 3.8 | 2.6 | 2.3 | 1.9 |
| Example 6 | 3.4 | 3.0 | 4.0 | 4.3 |
| Example 7 | 3.4 | 2.5 | 1.3 | 2.1 |
| Comparative Example 1 | 1.7 | 1.5 | 1.7 | 1.1 |
| Comparative Example 2 | 1.3 | 0.9 | 1.2 | 0.5 |
| Comparative Example 3 | 1.5 | 1.6 | 1.5 | 1.1 |
| Comparative Example 4 | 1.8 | 1.3 | 1.8 | 0.9 |
| Comparative Example 5 | 0.0 | 0.0 | 0.0 | 0.0 |
| Comparative Example 6 | 1.2 | 0.8 | 1.1 | 0.6 |
| Comparative Example 7 | 1.1 | 1.2 | 0.9 | 0.8 |

TABLE 4

| | Removal of Rate IL-6 [%] | Removal Rate of IL-8 [%] | Removal Rate of HMGB-1 [%] | Effect of Inhibition of Pulmonary Function Decline (P/F value after 6 hours) |
|---|---|---|---|---|
| Example 1 | 36 | 42 | 41 | 421 |
| Example 2 | 43 | 35 | 48 | 476 |
| Example 3 | 28 | 33 | 32 | 348 |
| Example 4 | 35 | 40 | 39 | 322 |
| Example 5 | 26 | 23 | 29 | 338 |
| Example 6 | 22 | 34 | 26 | 376 |
| Example 7 | 41 | 34 | 45 | — |
| Comparative Example 1 | 15 | 22 | 20 | 260 |
| Comparative Example 2 | 24 | 36 | 27 | 197 |
| Comparative Example 3 | 28 | 20 | 31 | 240 |
| Comparative Example 4 | 0 | 0 | 0 | 112 |

TABLE 4-continued

|  | Removal of Rate IL-6 [%] | Removal Rate of IL-8 [%] | Removal Rate of HMGB-1 [%] | Effect of Inhibition of Pulmonary Function Decline (P/F value after 6 hours) |
|---|---|---|---|---|
| Comparative Example 5 | 22 | 16 | 25 | 204 |
| Comparative Example 6 | 12 | 13 | 16 | 258 |
| Comparative Example 7 | 0 | 0 | 0 | 113 |

On the basis of the results of the above experiments, it is found that existing products (e.g., sepXiris®) that only remove the inflammatory cytokines have no effect for treating respiratory diseases, and the material for removing an activated leukocyte-activated platelet complex of the present invention can remove the activated leukocyte-activated platelet complex with high efficiency and is effective for treating respiratory diseases, especially for treating ARDS.

INDUSTRIAL APPLICABILITY

The column for removing blood components of the present invention has an ability for removing the activated leukocyte-activated platelet complexes, and therefore can be utilized as an extracorporeal circulation column for treating respiratory diseases, particularly for treating ARDS.

The invention claimed is:

1. A material for removing an activated leukocyte-activated platelet complex, the material being a water-insoluble carrier to the surface of which carrier a compound(s) having a charged functional group(s) is(are) bound,
    wherein an extending length ratio of said surface is 4 to 7.
2. The material for removing according to claim 1, wherein a center line mean roughness of said surface is 2 to 10 µm.
3. The material for removing according to claim 1, wherein the absolute value of charge amount of the functional group(s) is 0.3 to 3.0 mmol per 1 g dry weight of said water-insoluble carrier.
4. The material for removing according to claim 1, wherein said charged functional group is an amino group.
5. The material for removing according claim 1, wherein said water-insoluble carrier is in the form of fibers, and the fiber has a fiber diameter of 1 to 100 µm.
6. The material for removing according to claim 1, wherein said water-insoluble carrier comprises one or more polymers selected from the group consisting of polystyrene, polysulfone, and polyethersulfone.
7. The material for removing according to claim 1, wherein the material adsorbs and removes an activated leukocyte, IL-6, IL-8, or HMGB-1.
8. A column for blood purification, the column comprising the material for removing, according to claim 1.
9. A column for blood purification for treating a respiratory disease, the column comprising the material for removing, according to claim 1.

* * * * *